United States Patent
Altschul et al.

(10) Patent No.: US 9,320,747 B1
(45) Date of Patent: *Apr. 26, 2016

(54) SYSTEM AND METHOD FOR DIAGNOSIS AND TREATMENT

(71) Applicant: Pop Test Oncology Limited Liability Company, Cliffside Park, NJ (US)

(72) Inventors: Randice Lisa Altschul, Cliffside Park, NJ (US); Neil David Theise, New York, NY (US); Myron Rapkin, Indianapolis, IN (US); Rebecca O'Brien, Shell Knob, MO (US)

(73) Assignee: Pop Test Oncology Limited Liability Company, Cliffside Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/982,139

(22) Filed: Dec. 29, 2015

Related U.S. Application Data

(62) Division of application No. 14/100,714, filed on Dec. 9, 2013, now Pat. No. 9,114,147, which is a division of application No. 13/364,651, filed on Feb. 2, 2012, now Pat. No. 8,658,128.

(60) Provisional application No. 61/462,492, filed on Feb. 3, 2011, provisional application No. 61/463,212, filed on Feb. 14, 2011, provisional application No. 61/465,703, filed on Mar. 23, 2011, provisional application No. 61/518,248, filed on May 3, 2011, provisional application No. 61/519,323, filed on May 20, 2011.

(51) Int. Cl.
*A61K 31/58* (2006.01)
*A61K 31/45* (2006.01)
*A61K 31/337* (2006.01)

(52) U.S. Cl.
CPC .............. *A61K 31/58* (2013.01); *A61K 31/337* (2013.01)

(58) Field of Classification Search
IPC ........................................... A61K 31/58,31/337
See application file for complete search history.

(56) References Cited

U.S. PATENT DOCUMENTS

| | | | | |
|---|---|---|---|---|
| 8,658,128 B2 * | 2/2014 | Altschul | ................ | A61K 31/00 424/1.11 |
| 9,114,147 B2 * | 8/2015 | Altschul | ................ | A61K 31/00 |

* cited by examiner

*Primary Examiner* — Shirley V Gembeh
(74) *Attorney, Agent, or Firm* — Arthur Jacob

(57) ABSTRACT

This invention relates to a low cost rapid response diagnostic system to determine cortisol levels in patients selected as potential candidates for GCR (glucocorticoid receptor) antagonist therapy utilizing a GCR antagonist, such as ORG 34517. The rapid, sensitive, and inexpensive test can be used to determine patients who have non-normal cortisol production or disordered circadian rhythms as a method for selecting subjects for GCR antagonist therapy for whom it is likely to have beneficial and/or therapeutic effects, and can also be used to monitor changes in cortisol levels in response to treatment.

8 Claims, 8 Drawing Sheets

SYSTEM AND METHOD FOR DIAGNOSIS AND TREATMENT

CROSS-REFERENCE TO RELATED APPLICATIONS

This application is a Divisional application of U.S. Ser. No. 14/100,714 filed Dec. 9, 2013 which is a Divisional application of U.S. Ser. No. 13/364,651, filed Feb. 2, 2012, now U.S. Pat. No. 8,658,128, issued Feb. 25, 2014, which claims benefit under 35 U.S.C. §119(e) to U.S. Provisional Patent Application 61/462,492 filed Feb. 3, 2011; U.S. Provisional Patent Application 61/463,212 filed Feb. 14, 2011; U.S. Provisional Patent Application 61/465,703 filed Mar. 23, 2011; U.S. Provisional Patent Application 61/518,248 filed May 3, 2011; and U.S. Provisional Patent Application 61/519,323 filed May 20, 2011, the disclosures of which are incorporated herein in their entirety.

BACKGROUND OF THE INVENTION

1. Field of Invention

This invention relates to a low cost rapid response diagnostic system to determine cortisol levels in patients selected as potential candidates for GCR (glucocorticoid receptor) antagonist therapy utilizing a GCR antagonist, such as ORG 34517. The rapid, sensitive, and inexpensive test can be used to determine patients who have non-normal cortisol production or disordered circadian rhythms as a method for selecting subjects for GCR antagonist therapy for whom it is likely to have beneficial and/or therapeutic effects, and can also be used to monitor changes in cortisol levels in response to treatment.

2. Description of Related Art

ORG 34517 is one of a class of therapeutic agents designed to block the glucorticoid receptor (GR), acting as an antagonist for endogenous cortisol. Its primary developmental pathway has been as a treatment for neuropsychiatric diseases that are characterized by dysregulated signaling in the hypothalamic-pituitary-adrenal axis, often with higher than normal circulating levels of endogenous cortisol. Of particular note are the phase 2 clinical trials that have been completed for the treatment of psychotic depression. Other possible uses in this disease category which are under investigation include: post-traumatic stress disorder, weight gain in patients requiring long term anti-psychotic medication, hospital delirium of the elderly, etc. In addition, the diverse data indicate a possible role for GR-blockade as a means of promoting chemo-sensitization of target tumors. Pre-clinical trials demonstrate significant outcomes—breast cancer growth slowed and reversed. These are pre-clinical trials in which the company has successfully demonstrated the efficacy of a chemotherapy sensitizer for "triple negative" breast cancer.

The "triple negative" breast cancer is the most difficult to treat type of breast cancer, and is indicated by the patient testing negative for estrogen-receptor, progesterone-receptor and her-2/neu. The triple negative breast cancer is resistant to chemotherapy. Primary drug resistance and early onset of resistance are seen in other tumor types, as well, for example in liver and ovarian cancers, where there is a significant unmet medical need for effective therapy. Chemotherapy is still a key approach to cancer treatment. Chemosensitizers would contribute to improve the efficacy of current therapeutic drugs and potentially improve their side effect profile. The world cancer market was estimated at $23 billion in 2004 and is expected to grow to at least $61 billion by 2013 with a CAGR of 14.7%. U.S. Patent Application Publication no. 2011/0269728 (Pan et al.), incorporated by reference herein in its entirety, discloses a method of killing breast cancer cells comprising administering to a breast cancer patient an effective amount of a combination of anti-cancer compounds, wherein the anticancer compounds comprise a glucocorticoid receptor antagonist and a chemotherapeutic.

The present invention provides a low cost rapid response diagnostic system to determine salivary cortisol levels in patients selected as potential candidates for GCR (glucocorticoid receptor) antagonist therapy utilizing a GCR antagonist such as ORG 34517. The inventors have developed a saliva based diagnostic device for cortisol detection to accompany the development of ORG34517 as a therapeutic agent for multiple indications.

Clinical testing of cortisol levels in patients is a high cost, laborious test that can be salivary or serum, with samples taken from a patient and sent to a lab to await results. The cost and time factor for such tests has, to date, been prohibitive, preventing the rapid quantitative determination necessary to assign treatment with a glucocorticoid receptor (GCR) antagonist due to the inability to make the determinations of cortisol levels at point of need or to monitor changes in cortisol as a measure of treatment response. By allowing the physician to determine the elevated cortisol level of a patient and in turn provide a therapeutic for such elevation at point of measurement, the physician can qualify the best candidates suited for this type of therapeutic. The system also enables continual monitoring of the patient during treatment for assessment of responsiveness to treatment.

The present invention provides a system in which an apparatus uses a high void volume carrier to absorb sufficient amounts of saliva to then be placed into a reaction vessel with a reagent. The reagent is mixed with the sample and then is combined with, for example, a fluorescent ligand or pigment-labeled ligand and placed into a device to determine salivary cortisol levels of the patient in less than 5 minutes, in either a portable, miniaturized fluorescence polarization reader (in the former case) or into a lateral flow device (in the latter) for measuring amounts of substrate in a small amount of fluid by direct or indirect methods.

The reader apparatus, for example, provides temperature control and on-board mixing as an aid in viscosity control of the reaction to ensure better accuracy and precision.

The invention and method for non-invasive sampling and detecting the presence of a biological substance of interest in a test sample of, for example, saliva, or a bodily fluid, combining said test sample with a buffering system (Reagent 1) containing viscosity controllers and stabilizers in a reaction vessel, mix solution well, combining said test sample and buffering system mixture with a fluorescence-labeled ligand (Reagent 2) to said biological substance (assay solution) in a reaction vessel, mix solution well, and detecting a change of the assay solution in the fluorescence polarization reader, or a pigment labeled ligand.

The present invention relates to the use of glucocorticoid receptor (GCR) antagonists (e.g. ORG 34517) enabled by a device for rapidly, sensitively, specifically quantifying salivary cortisol levels as a surrogate for serum cortisol levels in a low cost manner. One purpose of this combination of inventions is to determine patients who have non-normal cortisol produced by the adrenal cortex or disordered circadian rhythms as a method for selecting subjects for GCR antagonist therapy for whom it is likely to have beneficial and/or therapeutic effects, i.e., those with abnormal high levels (but maintained circadian rhythm), over responsiveness to normal levels, high night-time cortisol levels as a feature of disrupted circadian rhythm. The rapid, sensitive, and inexpensive test can also be used to monitor changes in cortisol levels in response to treatment, in patients who have non-normal cortisol produced by the adrenal cortex or disordered circadian rhythms as a method for selecting subjects for GCR antagonist therapy for whom it is likely to have beneficial and/or therapeutic effects, but also in patients having normal baseline cortisol at the start of treatment, but for whom changing cortisol levels during treatment will indicate responsiveness to the GCR antagonist.

The endogenous glucocorticoids are steroids predominantly produced in the adrenal cortex. Glucocorticoids are important steroids for intermediary metabolism, immune, musculoskeletal, connective tissue and brain function. The main glucocorticoid in the body is cortisol. The production and secretion of cortisol is governed by a complex and highly efficient system that includes the hypothalamus, pituitary and the adrenal glands i.e., hypothalamic-pituitary-adrenal axis (HPA). Cortisol secretion has a circadian release rhythm with peak values in early morning and trough values at midnight.

The production and secretion of the most important glucocorticoid, cortisol, is governed by a complex and highly efficient system that includes the hypothalamus, pituitary and the adrenal glands i.e., hypothalamic-pituitary-adrenal axis. Cortisol secretion is regulated by the suprachiasmatic nucleus of the hypothalamus into a circadian release rhythm. The timing is synchronized with the solar day by dark-light shifts, which normally reflect the habitual sleep-wake pattern. Therefore in healthy persons, the cortisol secretion has a 24-hour circadian pattern with peak serum levels in the early morning, 3-6 hours after onset of sleep, and nadir levels around midnight. Physical and psychological stressors also activate cortisol secretion. Changed patterns of serum cortisol levels have been observed in connection with abnormal adrenocorticotropic hormone (ACTH), levels, clinical depression, psychological stress, and physiological stressors such as hypoglycemia, illness, fever, trauma, surgery, fear, pain, physical exertion, or temperature extremes. Cortisol levels and responsiveness may also differ from normal for elderly individuals and in individuals with autism or Asperger's syndrome.

Glucocorticoids (GCs) such as, in humans, cortisol, perform several important functions. These include participating in the regulation of carbohydrate, protein and fat metabolism by signaling the liver to make glucose and glycogen, the adipose tissues to release lipids and fatty acids into the bloodstream, and the skeletal muscles to release proteins or amino acids into the bloodstream. GCs also decrease bone formation.

GCs also regulate the body's inflammatory response as well. GCs are part of the feedback mechanism in the immune system that inhibits immune activity (i.e., inflammation). GCs cause their effects by binding to the GCR. The activated GCR complex in turn up-regulates the expression of anti-inflammatory proteins in the nucleus (a process known as transactivation) and represses the expression of pro-inflammatory proteins in the cytosol by preventing the translocation of other transcription factors from the cytosol into the nucleus (transrepression) (Rhen T and Cidlowski J A. NEJM 2005; 353: 1711-23).

GCR antagonist therapy is helpful in patients with abnormally high levels of cortisol (but maintained circadian rhythm), over responsiveness to normal levels, or high night time cortisol levels as a feature of disrupted circadian rhythm. Successful therapeutic use of such agents is thus dependent on determining circadian cortisol levels (either peak levels during the day, e.g., at noon, or measurements taken every 4 hours or 6 hours over a 24 hour period). This combined system of salivary cortisol quantification as an enabling device for its paired GCR antagonist will identify individuals for whom GCR antagonist therapy has a benefit.

The glucocorticoid receptor (GR) is expressed at high levels in some normal tissues, but not in others. Likewise, malignant tumors of diverse types and sites have variable GR expression. When present in normal or tumor (benign or malignant) tissues, this GR expression may be variously located in some or all of their cellular sub-compartments: 1. stem cells; 2. progenitor (so called "transit amplifying") cell descendents of activated stem cells; and 3. differentiated progeny of activated stem or progenitor cells.

As an example, in the gastrointestinal tract, GR are highly expressed in esophageal squamous epithelia, hepatocytes, and pancreatic islet cells, but are not highly expressed in other gastrointestinal epithelia (stomach, small and large intestines, pancreatic and biliary ducts). In corresponding malignancies arising in these epithelia, hepatocellular carcinoma (HCC) and squamous cell carcinomas (SCC) of the esophagus have consistently high GR expression. Gastric and colorectal adenocarcinomas have little to no GR expression.

Dexamethasone (DEX), a binding activator of GR, has been found to confer chemoresistance in oesophageal SCC and HCC cells, suggesting that GR expression may be biologically important in some GR-expressing carcinomas. This not only suggests why DEX or other glucocorticoids are not useful in treatment of these malignancies, but it implies that endogenous, circulating cortisol itself may actually promote chemoresistance, even in the absence of iatrogenic glucocorticoid administration. Therefore, these findings suggest that blockade of GR within such malignant tumors, by preventing activation by endogenous, circulating cortisol, can play a role in maintaining or promoting chemosensitivity and/or treating neoplasia.

The present invention therefore relates to the use of GR antagonists (e.g., ORG 34517, RU486, and others) for the treatment of, for example, esophageal SCC and HCC or other tumors with high GR expression as a means of inhibiting promotion of chemoresistance by endogenous cortisol. These effects may be present in all tumor cells or, when tumors have stem or progenitor cell compartments, these, specifically, as well. Thus, the present invention relates to the inhibition of chemoprevention in the bulk of cells making up a given tumor and/or in the rare stem/progenitor cells within the tumor that are often responsible for tumor resistance to therapy and re-occurrence, i.e., as a novel, targeted "cancer stem cell" treatment.

To avoid possible negative side effects of systemic blockade of GR, the present invention further relates to localized tumor treatment with GR antagonists through direct vascular infusion of tumor feeding vessels or by direct, intratumoral injection.

The present invention relates to the use of GR antagonists for the treatment of, for example, breast and other cancers. The invention is based on the observation that GR inhibition will increase tumor cell susceptibility. GR antagonists will block anti-apoptotic GR signaling in GR-overexpressing breast cancer cells and subsequently render breast cancer cells more susceptible to conventional and novel cytotoxic therapies (via blocking GR's pro-cell survival signaling pathway).

All references cited herein are incorporated herein by reference in their entireties.

BRIEF SUMMARY OF THE INVENTION

The present invention relates to a method for detecting the presence of a biological substance in a test sample, comprising the steps of: providing a test sample consisting of, for example, saliva, or a bodily fluid sample from a subject with, for example, a lollipop-like apparatus including a stem integrated with the base and a head integrated with the stem. The stem head includes a receptor of a sponge like carrier to ensure a high void volume to absorb sufficient saliva, oral fluid or a bodily fluid sample.

Combining the test sample with a buffering system (Reagent 1) containing viscosity controllers and stabilizers into a reaction vessel, mixing the solution well, and expressing all the liquid from the sample carrier apparatus into Reagent 1 in the reaction vessel and discarding. Reading the reaction vessel with sample and buffer for a fluorescence polarization blank and then combining the test sample and buffer mixture with a fluorescence-labeled ligand (Reagent 2) to said biological substance in the reaction vessel, mix solution well, to produce an assay solution. Furthermore, Reagent 2 may be delivered to the reaction vessel without further dilution volume of the assay solution.

The invention provides a method for screening a patient for a disease state suitable for GCR (glucocorticoid receptor) antagonist therapy, comprising the steps of: a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; and h) comparing the patient's measured cortisol levels to a predetermined reference range cortisol levels, wherein when the level of cortisol is elevated relative to the predetermined reference range, then the patient has a disease state which involves elevated cortisol, and thus has a disease state which is a potential candidate for GCR antagonist therapy. The invention further provides a method wherein the patient's test sample is selected from the group consisting of saliva, blood, plasma, serum, urine, other bodily fluids, and combinations thereof. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of about hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method further comprising the steps of: i) determining a patient's elevated cortisol level; and j) providing a therapeutic for such elevated cortisol level, wherein the therapeutic comprises GCR antagonist therapy. The invention further provides a method wherein the patient has changed patterns of cortisol levels that have been observed in connection with abnormal Adrenocorticotropic hormone (ACTH) levels. The invention further provides a method wherein the patient has non-normal cortisol levels produced by the adrenal cortex or disordered circadian rhythms, as a method for selecting subjects for GCR antagonist therapy wherein the patient has cortisol levels selected from the group consisting abnormally high cortisol levels but maintained circadian rhythm, over responsiveness to normal levels, and high night time cortisol levels as a feature of disrupted circadian rhythm. The invention further provides a method wherein the disease state is selected from the group consisting of cancer, clinical depression, psychological stress, and physiological stressors such as hypoglycemia, illness, fever, trauma, surgery, fear, pain, physical exertion, or temperature extremes.

The invention provides a method for monitoring changes in cortisol levels in response to treatment, in patients who have non-normal cortisol levels produced by the adrenal cortex, comprising: a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) administering a GCR antagonist; i) repeating steps a) to f) after the therapy has been administered; and j) determining the patient's circulating cortisol levels post-therapy, wherein when the cortisol levels change in response to treatment to indicate responsiveness to the GCR antagonist. The invention further provides a method wherein the patient's test sample is selected from the group consisting of saliva, blood, plasma, serum, urine, other bodily fluids, and combinations thereof. The invention further provides a method wherein the sample is obtained from the patient over more than one day, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means.

The invention provides a method for monitoring changes in cortisol levels in response to treatment and adjusting the treatment in response to these changes in a patient who has non-normal cortisol levels produced by the adrenal cortex, comprising: a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) administering a GCR antagonist; i) repeating steps a) to f) after the therapy has been administered; j) determining the patient's circulating cortisol levels post-therapy; and k) adjusting the GCR antagonist therapy in response to changes in the patient's cortisol levels post-therapy, wherein the adjustment in GCR antagonist therapy is to enhance therapeutic efficacy.

The invention further provides a method wherein the patient's test sample is selected from the group consisting of saliva, blood, plasma, serum, urine, other bodily fluids, and combinations thereof. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method wherein the GCR antagonist is selected from the group consisting of compounds which are selective for GCR, compounds which non-specifically bind steroid hormone receptors, and compounds which cross-react to both GCR and other steroid hormone receptors. The invention further provides a method wherein a decision to adjust the GCR antagonist therapy in response to changes in the cortisol levels, post-therapy, is made by a medical professional. The invention further provides a method further comprising the step of monitoring changes in biomarker expression using a nucleic acid microarray. The invention further provides a method wherein in the patients having normal baseline cortisol at the start of treatment, and changing cortisol levels during treatment indicate responsiveness to the GCR antagonist. The invention further provides a method wherein the combined system of salivary cortisol quantification as an enabling device for its paired GCR antagonist will identify patients for whom GCR antagonism has a likely benefit. The invention further provides a method wherein the GCR antagonist is selected from the group consisting of ORG 34517, 11-(substituted phenyl)-estra-4,9-diene derivatives, and 11-(substituted phenyl)-estra-4,9-diene derivatives of formula I

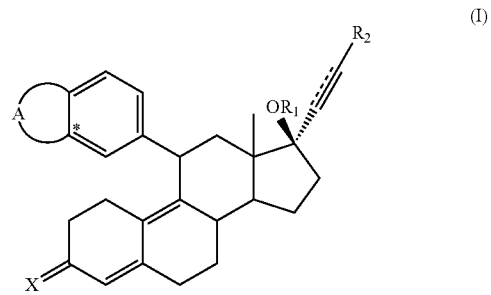

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; $R_1$ is H or 1-oxo(1-4C)alkyl; $R_2$ is H, (1-8C)alkyl, halogen or $CF_3$; X is selected from (H,OH), O, and NOH; and the interrupted line represents an optional bond. The invention further provides a method wherein the buffering system comprises additional components selected form the group consisting of viscosity controllers, stabilizers, and combinations thereof. The invention further provides a method wherein the fluorescence-labeled ligand which binds cortisol is selected from the group consisting of an aptamer, an antibody, an antibody fragment, a receptor, a receptor fragment, a binding polypeptide, a binding peptide, and combinations thereof. The invention further provides a method wherein the test sample is collected from the patient with a lollipop-like apparatus, including a stem integrated with the base and a head integrated with the stem, and further wherein the stem head including a receptor of a sponge like carrier to ensure a high void volume to absorb sufficient sample.

The invention provides a method of treating major depressive disorder in a patient in need thereof by determining whether the patient has major depressive disorder suitable for GCR (glucocorticoid receptor) antagonist therapy, comprising the steps of a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) comparing the measured cortisol levels to a predetermined reference range cortisol levels, wherein when the level of cortisol is elevated relative to the a predetermined reference range, then the patient has major depressive disorder which involves elevated cortisol, and thus has major depressive disorder suitable for GCR (glucocorticoid receptor) antagonist therapy; and i) when the patient has major depressive disorder suitable for GCR antagonist therapy, a administering at least one GCR antagonist. The invention further provides a method wherein the patient's test sample is selected from the group consisting of saliva, blood, plasma, serum, urine, other bodily fluids, and combinations thereof. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method wherein the GCR (glucocorticoid receptor) antagonist is selected from the group consisting of ORG 34517, 11-(substituted phenyl)-estra-4,9-diene derivatives, and 11-(substituted phenyl)-estra-4,9-diene derivatives of formula I

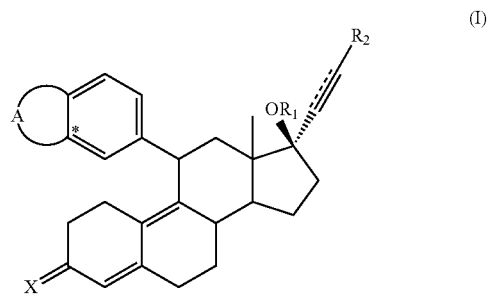

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond.

The invention provides a method of treating psychotic depression in a patient in need thereof by determining whether the patient has psychotic depression suitable for GCR (glucocorticoid receptor) antagonist therapy, comprising the steps of a) obtaining a test sample from the patient, optionally at a predetermined time using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) comparing the measured cortisol levels to a predetermined reference range cortisol levels, wherein when the level of cortisol is elevated relative to the predetermined reference range, then the patient has psychotic depression which involves elevated cortisol, and thus has psychotic depression suitable for GCR antagonist therapy; and i) when the patient has psychotic depression suitable for GCR antagonist therapy, administering at least one GCR antagonist. The invention further provides a method wherein the patient's test sample is selected from the group consisting of saliva, blood, plasma, serum, urine, other bodily fluids, and combinations thereof. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method wherein the GCR antagonist is selected from the group consisting of ORG 34517, 11-(substituted phenyl)-estra-4,9-diene derivatives, and 11-(substituted phenyl)-estra-4,9-diene derivatives of formula I

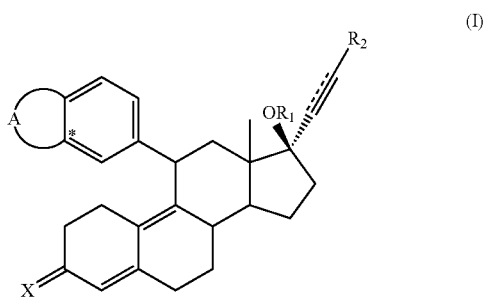

(I)

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond.

The invention provides a method of treating stress-induced cortisol elevation in a patient in need thereof by determining whether the patient has stress-induced cortisol elevation suitable for GCR (glucocorticoid receptor) antagonist therapy, comprising the steps of: a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex;

f) comparing the measurement of the assay solution relative to the blank measurement; g) determining the patient's circulating cortisol levels based on the change of the measurement; h) comparing the measured cortisol levels to a predetermined reference range cortisol levels, wherein when the level of cortisol is elevated relative to the predetermined reference range, then the patient has stress-induced cortisol elevation which involves elevated cortisol, and thus has stress-induced cortisol elevation suitable for GCR antagonist therapy; and i) when the patient has stress-induced cortisol elevation suitable for GCR antagonist therapy, administering at least one GCR antagonist. The invention further provides a method wherein the patient's test sample is selected from the group consisting of saliva, blood, plasma, serum, urine, other bodily fluids, and combinations thereof. The invention further provides a method wherein the stress-related cortisol elevation is related to a hospital stay, medical treatment, an institutional stay, clinical depression, psychological stress, physiological stressors, hypoglycemia, illness, fever, trauma, surgery, fear, pain, physical exertion, or temperature extremes. The invention further provides a method wherein the patient is an elderly individual. The invention further provides a method wherein the patient has autism or Asperger's syndrome. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method wherein the GCR antagonist is selected from the group consisting of ORG 34517, 11-(substituted phenyl)-estra-4,9-diene derivatives, and 11-(substituted phenyl)-estra-4,9-diene derivatives of formula I

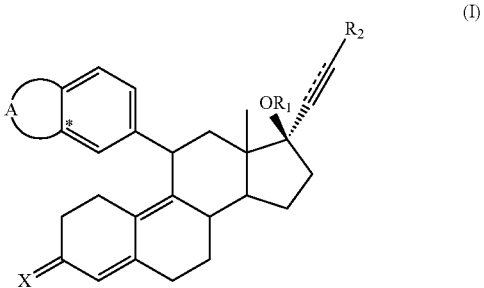

(I)

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond.

The invention provides a method of treating post-traumatic stress disorder in a patient in need thereof by determining whether the patient has post-traumatic stress disorder suitable for GCR (glucocorticoid receptor) antagonist therapy, comprising the steps of: a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; comparing the measurement of the assay solution relative to the blank measurement; g) determining the patient's circulating cortisol levels based on the change of the measurement; h) comparing the measured cortisol levels to a predetermined reference range cortisol levels, wherein when the level of cortisol is elevated relative to the predetermined reference range, then the patient has post-traumatic stress disorder which involves elevated cortisol, and thus has post-traumatic stress disorder suitable for GCR (glucocorticoid receptor) antagonist therapy; and i) when the patient has post-traumatic stress disorder suitable for GCR antagonist therapy, administering at least one GCR antagonist. The invention further provides a method wherein the patient's test sample is selected from the group consisting of saliva, blood, plasma, serum, urine, other bodily fluids, and combinations thereof. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method wherein the GCR antagonist is selected from the group consisting of ORG 34517, 11-(substituted phenyl)-estra-4,9-diene derivatives, and 11-(substituted phenyl)-estra-4,9-diene derivatives of formula I

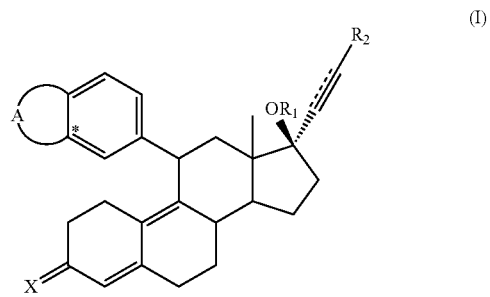

(I)

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond.

The invention provides a method of prevention of weight gain in patients using anti-psychotic or anti-depressant medications in a patient in need thereof, wherein the weight gain is suitable for GCR (glucocorticoid receptor) antagonist therapy, comprising the steps of a) obtaining a test sample from the patient, optionally at a predetermined time using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) comparing the measured cortisol levels to a predetermined reference range cortisol levels, wherein when the level of cortisol is elevated relative to the predetermined reference range, then the patient has weight gain which involves elevated cortisol, which is suitable for GCR (glucocorticoid receptor) antagonist therapy; and i) when the patient has weight gain suitable for GCR antagonist therapy, administering at least one GCR antagonist. The invention further provides a method wherein the patient's test sample is selected from the group consisting of saliva, blood, plasma, serum, urine, other bodily fluids, and combinations thereof. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method wherein the GCR antagonist is selected from the group consisting of ORG 34517, 11-(substituted phenyl)-estra-4,9-diene derivatives, and 11-(substituted phenyl)-estra-4,9-diene derivatives of formula I

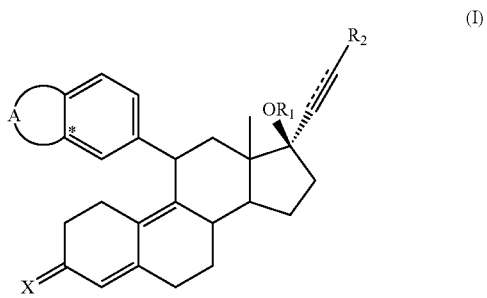

(I)

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond.

The invention provides a method of treating Cushing's syndrome in a patient in need thereof by determining whether the patient has Cushing's syndrome suitable for GCR (glucocorticoid receptor) antagonist therapy, comprising the steps of a) obtaining a test sample from the patient, optionally at a predetermined time, using a test sample collection unit; b) combining said test sample with a buffering system to form a mixture in a reaction unit; c) measuring a parameter of the mixture to determine a blank measurement; d) combining said test sample and buffer mixture with a labeled ligand which binds cortisol, wherein the labeled ligand is provided in a label unit, in the reaction unit to produce an assay solution; or combining said test sample and buffer mixture and delivering it to a carrier containing a labeled ligand which binds cortisol, wherein the labeled ligand is provided in a label unit, in the reaction unit to produce an assay immobilized complex; e) measuring a parameter of said assay solution or complex; f) comparing the measurement of the assay solution relative to the blank measurement; g) determining the patient's circulating cortisol levels based on the change of the measurement; h) comparing the measured cortisol levels to a predetermined reference range cortisol levels, wherein when the level of cortisol is elevated relative to the predetermined reference range, then the patient has Cushing's syndrome which involves elevated cortisol, which is suitable for GCR (glucocorticoid receptor) antagonist therapy; and i) when the patient has Cushing's syndrome suitable for GCR antagonist therapy, administering at least one GCR antagonist. The invention further provides a method wherein the patient's test sample is selected from the group consisting of saliva, blood, plasma, serum, urine, other bodily fluids, and combinations thereof. The invention further provides a method wherein the sample is obtained from the patient over more than one time, and the predetermined time is selected from the group consisting of morning, noon, and evening. The invention further provides a method wherein the sample is obtained from the patient over consecutive days. The invention further provides a method wherein the method is to determine the circadian cycle of the cortisol levels in the patient, and the predetermined time is selected from the group consisting of hourly, every 4 hours, every 6 hours, every 8 hours, and every 12 hours. The invention further provides a method wherein the sample is obtained from the patient over consecutive days. The invention further provides a method wherein the predetermined reference range is a medically standard reference range. The invention further provides a method wherein the predetermined reference range is the patient's previously measured level. The invention further provides a method wherein the ligand is detectably labeled with a moiety selected from the group consisting of a radioisotope, a fluorophore, a quencher of fluorescence, an enzyme, an affinity tag, and an epitope tag. The invention further provides a method wherein said measuring of said parameter of said mixture and said assay solution is performed using a method selected from spectroscopic, photochemical, radiochemical, biochemical, enzymatic, immunochemical, chemical label displacement, surface plasmon resonance, fluorescence resonance energy transfer, fluorescence quenching, lateral flow, and fluorescence polarization means. The invention further provides a method wherein the GCR antagonist is selected from the group consisting of ORG 34517, 11-(substituted phenyl)-estra-4,9-diene derivatives, and 11-(substituted phenyl)-estra-4,9-diene derivatives of formula I

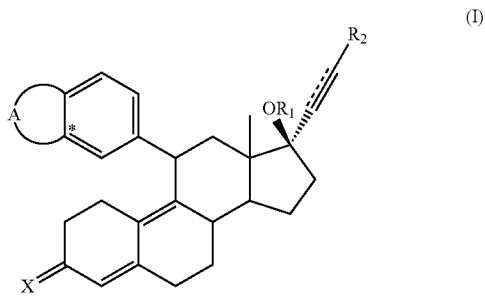

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond.

The invention provides a pharmaceutical composition comprising: (a) GCR (glucocorticoid receptor) antagonist; (b) the pharmaceutical composition of (a), further comprising at least one pharmaceutically acceptable excipient; (c) the pharmaceutical composition of (a) or (b), wherein the pharmaceutical composition is formulated or manufactured as a liquid, an elixir, an aerosol, a spray, a powder, a tablet, a pill, a capsule, a gel, a geltab, a nanosuspension, a nanoparticle, an extended release dosage form, or a topical formulation. The invention provides a method for treating a condition selected from the group consisting of major depressive disorder, psychotic depression, stress-induced cortisol elevation, post-traumatic stress disorder, preventing weight gain in patients using anti-psychotic and anti-depressant medications, or having Cushing's syndrome, in a patient in need of such treatment comprising administering the pharmaceutical composition to the patient.

The invention provides a kit for the treatment, amelioration or prevention of a condition selected from the group consisting of major depressive disorder, psychotic depression, stress-induced cortisol elevation, post-traumatic stress disorder, preventing weight gain in patients using anti-psychotic and anti-depressant medications, or having Cushing's syndrome, in a patient in need of such treatment comprising: (a) the pharmaceutical composition; and (b) at least one blister package; a lidded blister; a blister card or packet; a clamshell; an intravenous (IV) package, IV packette or IV container; a tray or a shrink wrap comprising the pharmaceutical composition of (a) and instructions for use of the pharmaceutical composition.

The invention provides a product of manufacture comprising a blister package; a lidded blister; a blister card or packet; a clamshell; an intravenous (N) package, N packette or IV container; a tray or a shrink wrap comprising the pharmaceutical composition and instructions for use of the pharmaceutical composition. The invention further provides a method wherein the GCR (glucocorticoid receptor) antagonist selected from the group consisting of ORG 34517, 11-(substituted phenyl)-estra-4,9-diene derivatives, and 11-(substituted phenyl)-estra-4,9-diene derivatives of formula I

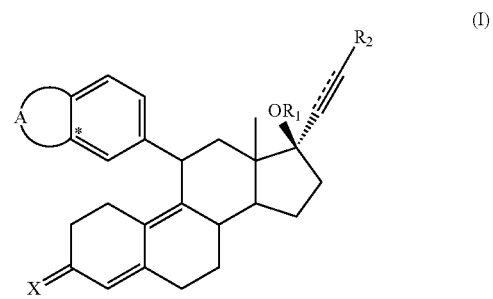

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond.

The invention provides a method for treating neoplasia characterized by expression of a glucocorticoid receptor, in a patient in need of such treatment, comprising: administering to said animal or human therapeutically effective amounts of each of at least one neoplasia-treating agent and a GCR (glucocorticoid receptor) antagonist selected from the group consisting of ORG 34517, 11-(substituted phenyl)-estra-4,9-diene derivatives, and 11-(substituted phenyl)-estra-4,9-diene derivatives of formula I

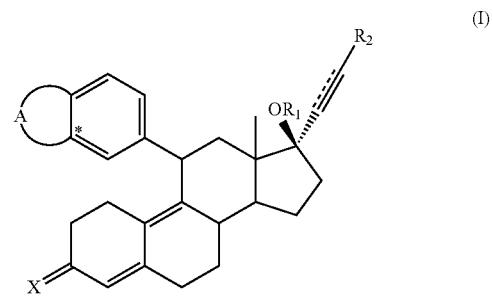

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond. The invention further provides a method wherein ORG34517 is administered as an agent which directly effects tumor growth, independent of other administered treatment modalities, for palliation, remission, or cure. The invention further provides a method wherein said neoplasia treating agent is radiation. The invention further provides a method wherein said neoplasia treating agent is a biotherapy agent. The invention further provides a method wherein said neoplasia treating agent is a chemotherapy agent. The invention further provides a method wherein said neoplasia treating agent is a radionuclide. The invention further provides a method wherein the neoplasia is selected for the group consisting of hepatocellular carcinoma, esophageal squamous cell carcinoma, breast cancer, pancreatic cancer, squamous cell cancer or adenocarcinoma of the head and neck, colorectal cancer, renal cancer, brain cancer, prostate cancer, small and non-small cell lung cancer, bladder cancer, bone or joint cancer, uterine cancer, cervical cancer, multiple myeloma, hematopoietic malignancies, lymphoma, Hodgkin's disease, non-Hodgkin's lymphoma, skin cancer, melanoma, squamous cell carcinoma, leukemia, lung cancer, ovarian cancer, stomach cancer, Kaposi's sarcoma, laryngeal cancer, endocrine carcinomas, cancer of the thyroid gland, cancer of the parathyroid gland, cancer of the pituitary gland, cancer of the adrenal gland, and combinations thereof. The invention further provides a method wherein the neoplasia expresses multidrug resistance genes when GR is activated through binding by endogenous cortisol. The invention further provides a method wherein the neoplasia expresses proteins of cell survival pathway (including inhibition of apoptosis) genes when GR is activated through binding by endogenous cortisol. The invention further provides a method wherein the neoplasia expresses genes responsible for epithelial-mesenchymal transition and cell shape maintenance are repressed when GR is activated through binding by endogenous cortisol. The invention further provides a method wherein the neoplasia expresses genes involved in signal transduction pathways, lipid/fatty acid metabolism, inflammation and macrophage regulation, transcriptional regulation and chromatin remodeling, and cell metabolic pathways. The invention further provides a method wherein tumor stem cells (TSC) express GR, blockade of which by ORG34517 results in anti-TSC therapy. The invention further provides a method wherein TSC express multidrug resistance genes when GR is activated through binding by endogenous cortisol. The invention further provides a method wherein TSC express proteins of cell survival pathways (including inhibition of apoptosis) genes when GR is activated through binding by endogenous cortisol. The invention further provides a method wherein TSC express genes responsible for epithelial-mesenchymal transition and cell shape maintenance are repressed when GR is activated through binding by endogenous cortisol. The invention further provides a method wherein TSC express genes involved in signal transduction pathways, lipid/fatty acid metabolism, inflammation and macrophage regulation, transcriptional regulation and chromatin remodeling, and cell metabolic pathways. The invention further provides a method wherein the neoplasia is chemo-resistant ER/GR+ breast cancer. The invention further provides a method wherein the administration of ORG 34517 for GR-blockade, reduces toxicities and side effects when given systemically. The invention further provides a method wherein the ORG 34517 given systemically through oral or intravenous routes. The invention further provides a method wherein the ORG 34517 is targeted to tumor by intra-arterial infusion to reduce systemic side effects of GR blockade. The invention further provides a method wherein the ORG 34517 is given to accomplish cure or remission of tumor. The invention further provides a method wherein the ORG 34517 is given to accomplish reduction of tumor burden to enhance effectiveness of subsequent surgical resection. The invention further provides a method wherein the ORG 34517 is given to accomplish reduction of tumor burden to make an unresectable tumor resectable.

The invention provides a method for treatment of neoplasia in a patient comprising targeted delivery of ORG 34517, wherein the neoplasia expresses multidrug resistance genes when GR is activated through binding by endogenous cortisol. The invention further provides a method wherein the HCC patient is not a candidate to undergo surgical intervention because tumor is too large or encroaches on liver anatomy in a manner that prevents resection, delivery of ORG34517 prior to ablative or chemotherapy to shrink the tumor and make it resectable. The invention further provides a method wherein the HCC is present in cirrhosis and the patient is not a candidate for transplantation because of large tumor size, administration of ORG34517 making the tumor amenable to ablative or chemotherapy to shrink the tumor and allow the patient to be eligible for liver transplant. The invention further provides a method wherein the HCC is present in cirrhosis and the patient is a candidate for transplantation, administration of ORG34517 making the tumor amenable to ablative therapy to manage tumor while patient remains on the liver transplant waitlist.

The invention provides a method for low toxicity chemo-prevention by targeted liver infusion in patients with forms of established cirrhosis that are high risk for emergence of HCC, including those with premalignant lesions diagnosed on biopsy or by radiology, comprising targeted delivery of Org34517 to intrahepatic lesions, wherein the targeted delivery of ORG g34517 to intrahepatic lesions prevents emergence of HCC. The invention further provides a method wherein the patient with HCC is not a candidate for undergo surgical intervention. The invention further provides a method wherein the HCC resides in locations where surgical or ablative interventions are not available. The invention further provides a method wherein the patient with HCC has cirrhosis that is too advanced to make partial hepatectomy safe. The invention further provides a method wherein the patient with HCC is too early in their chronic liver disease to qualify for transplantation. The invention further provides a method wherein the HCC is too advanced for localized treatments.

The invention provides a method for treatment of HCC comprising: a) targeted delivery of ORG 34517 to intrahepatic lesions, wherein the targeted delivery of ORG 34517 to intrahepatic lesions improves outcomes of localized chemoablative therapies. The invention further provides a method wherein the treatment is to help patients qualify for liver transplantation.

The invention provides a method for low toxicity chemo-prevention by targeted liver infusion in patients with forms of established cirrhosis that are high risk for emergence of HCC, including those with premalignant lesions diagnosed on biopsy or by radiology comprising targeted delivery of ORG 34517 to intrahepatic lesions, wherein the targeted delivery of ORG 34517 to intrahepatic lesions prevents emergence of HCC. The invention further provides a method wherein the neoplasia is eSCC.

The invention provides a method for treatment of eSCC in a patient with unresectable eSCC where systemic or targeted administration of ORG 34517 makes tumor responsive to ablative or chemotherapies as palliative or curative treatment.

The invention provides method for treatment of eSCC in a patient with unresectable eSCC where systemic or targeted administration of ORG 34517 makes tumor responsive to ablative or chemotherapies to shrink the tumor and enhance resectability. The invention further provides a method wherein the neoplasia-treating agent is a chemotherapeutic agent including but not limited to gemcitabine, paclitaxel, carboplatin, cisplatin, and 5-fluorouracil. The invention further provides a method wherein the therapeutic effective amount of glucocorticoid administered is about 100 to 400 microg/kg body weight per day when administered intravenously.

The invention provides a method for treating neoplasia, in an animal or human in need of such treatment, wherein said neoplasia comprises neoplastic stem cells characterized by expression of a glucocorticoid receptor, and further characterized by expression of multidrug resistance genes or other stem cell related means of survival when GR is activated through binding by endogenous cortisol, the method comprising: a) administering to said animal or human a therapeutically effective amount of ORG 34517; and b) administering to said animal or human a therapeutically effective amount of the at least one neoplasia-treating agent, wherein said therapeutically effective amount of ORG 34517 is an amount sufficient to promote susceptibility of the neoplastic stem cells to at least one neoplasia-treating agent. The invention further provides a method wherein said neoplasia-treating agent is radiation selected from the group consisting of external beam or radionuclide therapy. The invention further provides a method wherein said neoplasia-treating agent is a biotherapy agent. The invention further provides a method wherein said neoplasia-treating agent is a chemotherapy agent. The invention further provides a method wherein said neoplasia-treating agent is a radionuclide. The invention further provides a method wherein the neoplasia is selected from the group consisting of hepatocellular carcinoma, esophageal squamous cell carcinoma, breast cancer, pancreatic cancer, squamous cell cancer or adenocarcinoma of the head and neck, colorectal cancer, renal cancer, brain cancer, prostate cancer, small and non-small cell lung cancer, bladder cancer, bone or joint cancer, uterine cancer, cervical cancer, multiple myeloma, hematopoietic malignancies, lymphoma, Hodgkin's disease, non-Hodgkin's lymphoma, skin cancer, melanoma, squamous cell carcinoma, leukemia, lung cancer, ovarian cancer, stomach cancer, Kaposi's sarcoma, laryngeal cancer, endocrine carcinomas, cancer of the thyroid gland, cancer of the parathyroid gland, cancer of the pituitary gland, cancer of the adrenal gland, and combinations thereof. The invention further provides a method wherein the neoplasia expresses multidrug resistance genes when GR is activated through binding by endogenous cortisol.

The invention provides a pharmaceutical composition for treating neoplasia in a patient which is characterized by expression of a glucocorticoid receptor, comprising: a) therapeutically effective amounts of at least one neoplasia-treating agent; b) a GCR (glucocorticoid receptor) antagonist selected from the group consisting of ORG 34517, 11-(substituted phenyl)-estra-4,9-diene derivatives, and 11-(substituted phenyl)-estra-4,9-diene derivatives of formula I

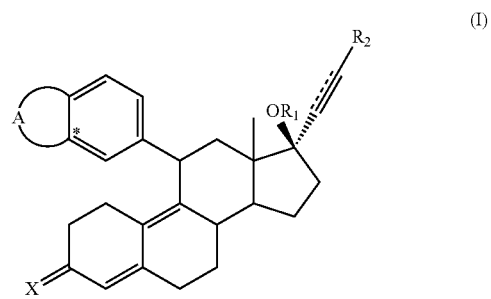

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond; and c) optionally, at least one pharmaceutically acceptable carrier. The invention further provides a method wherein said neoplasia-treating agent is selected from the group consisting of a chemotherapeutic agent, a biotherapeutic agent, a radionuclide agent, and combinations thereof. The invention further provides a method wherein the neoplasia is selected from the group consisting of hepatocellular carcinoma, esophageal squamous cell carcinoma, breast cancer, pancreatic cancer, squamous cell cancer or adenocarcinoma of the head and neck, colorectal cancer, renal cancer, brain cancer, prostate cancer, small and non-small cell lung cancer, bladder cancer, bone or joint cancer, uterine cancer, cervical cancer, multiple myeloma, hematopoietic malignancies, lymphoma, Hodgkin's disease, non-Hodgkin's lymphoma, skin cancer, melanoma, squamous cell carcinoma, leukemia, lung cancer, ovarian cancer, stomach cancer, Kaposi's sarcoma, laryngeal cancer, endocrine carcinomas, cancer of the thyroid gland, cancer of the parathyroid gland, cancer of the pituitary gland, cancer of the adrenal gland, and combinations thereof. The invention further provides a method, wherein the neoplasia is chemo-resistant ER-GR+ breast cancer. The invention further provides a method wherein the neoplasia expresses multidrug resistance genes when GR is activated through binding by endogenous cortisol. The invention further provides a method wherein the chemotherapeutic agent is selected from the group comprising: busulfan, cisplatin, carboplatin, chlorambucil, cyclophosphamide, ifosfamide, dacarbazine (DTIC), mechlorethamine (nitrogen mustard), melphalan carmustine (BCNU) lomustine (CCNU), 5-FU, capecitabine, methotrexate, gemcitabine, cytarabine (ara-C), fludarabine dactinomycin, daunorubicin, doxorubicin (Adriamycin), idarubicin, mitoxantrone, paclitaxel, docetaxel, etoposide (VP-16), vinblastine, vincristine, vinorelbine prednisone, dexamethasone, tamoxifen, fulvestrant, anastrozole, letrozole, megestrol acetate, bicalutamide, flutamide, leuprolide, goserelin, L-asparaginase, and tretinoin, gemcitabine, paclitaxel, carboplatin, 5-FU, and combinations thereof.

The invention provides a diagnostic kit comprises the following components: a) test sample collection unit; b) the buffer system unit; c) the reaction unit; and d) the label unit, wherein the components are in a blister package; a lidded blister; a blister card or packet; a clamshell; a tray, or a shrink wrap, and instructions for use of the kit. The invention further provides test sample collection unit wherein the test sample collection unit comprises a stem integrated with a base, and a head integrated with the stem. The invention further provides a test sample collection unit wherein the stem head comprises a receptor of a sponge-like carrier sufficient to ensure a high void volume to absorb sufficient saliva, oral fluid or a bodily fluid sample. The invention further provides a buffer system unit wherein the buffer system unit comprises additional components selected from the group consisting of viscosity controllers, stabilizers, and combinations thereof. The invention further provides a reaction unit wherein the reaction unit is adapted to fit in a fluorescent polarization reader. The invention further provides a label unit wherein the label unit comprises a fluorescence-labeled ligand which binds cortisol, wherein the fluorescence-labeled ligand which binds cortisol is selected from the group consisting of an aptamer, an antibody, an antibody fragment, a receptor, a receptor fragment, a binding polypeptide, a binding peptide, and combinations thereof. The invention further provides a diagnostic kit wherein the reader apparatus provides temperature control and on-board mixing as an aid in viscosity control of the reaction to ensure better accuracy and precision. The invention further provides a diagnostic kit wherein the reader is a miniaturized, portable apparatus for measuring fluorescence polarization of a liquid sample by direct or indirect methods. The invention further provides a diagnostic kit wherein system also enables continual monitoring of the patient during treatment for assessment of responsiveness to treatment.

BRIEF DESCRIPTION OF SEVERAL VIEWS OF THE DRAWINGS

The invention will be described in conjunction with the following drawings in which like reference numerals designate like elements and wherein:

FIG. 4A shows a blister pack of reagent cartridge units. FIG. 4B shows an exemplary reaction vessel and cap. FIG. 4C shows an exemplary sample carrier. FIG. 4D shows an exemplary reagent 2 (fluorescent ligand) carrier.

FIG. 5A shows an exemplary sample carrier. FIG. 5B shows an exemplary reaction vessel and cap. FIG. 5C shows an exemplary reagent 2 (fluorescent ligand) carrier.

FIG. 6A shows an exemplary sample carrier. FIG. 6B shows an exemplary reagent 2 (fluorescent ligand) carrier.

DETAILED DESCRIPTION OF THE INVENTION

Figure 1:
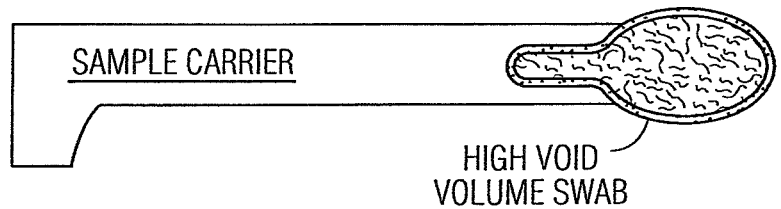
FIG. 1 is an example of a sample carrier.

This invention relates to a low cost rapid response diagnostic system to determine salivary cortisol levels in patients selected as potential candidates for GCR (glucocorticoid receptor) antagonist therapy utilizing a GCR antagonist, such as ORG 34517. The rapid, sensitive, and inexpensive test can be used to determine patients who have non-normal cortisol production or disordered circadian rhythms as a method for selecting subjects for GCR antagonist therapy for whom it is likely to have beneficial and/or therapeutic effects, and can also be used to monitor changes in cortisol levels in response to treatment.

As used herein, the term "agent" refers to any molecule, compound, methodology and/or substance for use in the prevention, treatment, management and/or diagnosis of cancer. Non-limiting examples of cancer therapies include chemotherapies, radiation therapies, hormonal therapies, anti-angiogenesis therapies, targeted therapies, and/or biological therapies including immunotherapies and surgery As used herein, the term "cancer cells" refer to cells that acquire a characteristic set of functional capabilities during their development, including the ability to evade apoptosis, self-sufficiency in growth signals, insensitivity to anti-growth signals, tissue invasion/metastasis, significant growth potential, and/or sustained angiogenesis. The term "cancer cell" is meant to encompass both pre-malignant and malignant cancer cells.

As used herein, the term "cancer stem cell(s)" refers to a cell that can be a progenitor of a highly proliferative cancer cell. A cancer stem cell has the ability to re-grow a tumor as demonstrated by its ability to form tumors in immunocompromised mice, and typically to form tumors upon subsequent serial transplantation in immunocompromised mice. Cancer stem cells are also typically slow-growing relative to the bulk of a tumor; that is, cancer stem cells are generally quiescent. In certain embodiments, but not all, the cancer stem cell may represent approximately 0.1 to 10% of a tumor.

As used herein, the phrase "diagnostic agent" refers to any molecule, compound, and/or substance that is used for the purpose of diagnosing a disease or condition. Non-limiting examples of diagnostic agents include antibodies, antibody fragments, or other proteins, including those conjugated to a detectable agent. As used herein, the term "detectable agents" refer to any molecule, compound and/or substance that is detectable by any methodology available to one of skill in the art. Non-limiting examples of detectable agents include dyes, gases, metals, or radioisotopes. As used herein, diagnostic agent and "imaging agent" are equivalent terms.

As used herein, the term "effective amount" refers to the amount of a therapy that is sufficient to result in the prevention of the development, recurrence, or onset of a disease or condition, such as cancer, and one or more symptoms thereof, to enhance or improve the prophylactic effect(s) of another therapy, reduce the severity, the duration of a disease or condition, such as cancer, ameliorate one or more symptoms of a disease or condition, such as cancer, prevent the advancement of a disease or condition, such as cancer, cause regression of a disease or condition, such as cancer, and/or enhance or improve the therapeutic effect(s) of another therapy.

In an embodiment of the invention, the amount of a therapy is effective to achieve one, two, three, or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; (12) an increase in the number of patients in remission; (13) an increase in the length or duration of remission; (14) a decrease in the recurrence rate of cancer; (15) an increase in the time to recurrence of cancer; and (16) an amelioration of cancer-related symptoms and/or quality of life.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the term "predetermined reference range" refers to a reference range for the particular biological entity, e.g., cortisol, for a subject or a population of subjects. Each laboratory may establish its own reference range for each particular assay, or a standard reference range for each assay may be made available and used locally, regionally, nationally, or worldwide or may be patient-specific. In one specific embodiment, the term refers to a reference range for the amount of cortisol in a patient or a specimen from a patient. In another specific embodiment, the term refers to a reference range for the amount of cortisol in a patient or a specimen from a patient.

As used herein, the terms "prevent," "preventing" and "prevention" in the context of the administration of a therapy to a subject refer to the prevention or inhibition of the recurrence, onset, and/or development of a disease or condition, such as cancer or a symptom thereof in a subject resulting from the administration of a therapy (e.g., a prophylactic or therapeutic agent), or a combination of therapies (e.g., a combination of prophylactic or therapeutic agents). In some embodiments, such terms refer to one, two, three, or more results following the administration of one or more therapies: (1) a stabilization, reduction or elimination of the cancer stem cell population; (2) a stabilization, reduction or elimination in the cancer cell population; (3) an increase in response rate; (4) an increase in the length or duration of remission; (5) a decrease in the recurrence rate of cancer; (6) an increase in the time to recurrence of cancer; (7) an increase in the disease-free, relapse-free, progression-free, and/or overall survival of the patient; and (8) an amelioration of cancer-related symptoms and/or quality of life. In specific embodiments, such terms refer to a stabilization, reduction or elimination of the cancer stem cell population.

As used herein, the terms "subject" and "patient" are used interchangeably. As used herein, the term "patient" refers to an animal, preferably a mammal such as a non-primate (e.g., cows, pigs, horses, cats, dogs, rats etc.) and a primate (e.g., monkey and human), and most preferably a human. In some embodiments, the subject is a non-human animal such as a farm animal (e.g., a horse, pig, or cow) or a pet (e.g., a dog or cat). In a specific embodiment, the subject is an elderly human. In another embodiment, the subject is a human adult. In another embodiment, the subject is a human child. In yet another embodiment, the subject is a human infant.

As used herein, the term "therapeutic agent" refers to any molecule, compound, and/or substance that is used for the purpose of treating and/or managing a disease or disorder. Examples of therapeutic agents include, but are not limited to, proteins, immunoglobulins (e.g., multi-specific Igs, single chain Igs, Ig fragments, polyclonal antibodies and their fragments, monoclonal antibodies and their fragments), peptides (e.g., peptide receptors, selectins), binding proteins, biologics, chemospecific agents, chemotoxic agents (e.g., anti-cancer agents), proliferation-based therapy, radiation, chemotherapy, anti-angiogenic agents, and small molecule drugs.

As used herein, the terms "therapies" and "therapy" can refer to any method(s), composition(s), and/or agent(s) that can be used in the prevention, treatment and/or management of a disease or condition, such as cancer, or one or more symptoms thereof. In certain embodiments, the terms "therapy" and "therapies" refer to chemotherapy, small molecule therapy, radioimmunotherapy, toxin therapy, prodrug-activating enzyme therapy, biologic therapy, antibody therapy, surgical therapy, hormone therapy, immunotherapy, anti-angiogenic therapy, targeted therapy, epigenetic therapy, demethylation therapy, histone deacetylase inhibitor therapy, differentiation therapy, radiation therapy, or a combination of the foregoing and/or other therapies useful in the prevention, management and/or treatment of a cancer or one or more symptoms thereof.

As used herein, the terms "treat," "treatment," and "treating" in the context of the administration of a therapy to a subject refer to the reduction or inhibition of the progression and/or duration of a disease or condition, such as cancer, the reduction or amelioration of the severity of a disease or condition, such as cancer, and/or the amelioration of one or more symptoms thereof resulting from the administration of one or more therapies. In specific embodiments, such terms refer to one, two or three or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; and (12) an increase in the number of patients in remission. In certain embodiments, such terms refer to a stabilization or reduction in the cancer stem cell population. In some embodiments, such terms refer to a stabilization or reduction in the growth of cancer cells. In some embodiments, such terms refer to a stabilization or reduction in the cancer stem cell population and a reduction in the cancer cell population. In some embodiments, such terms refer to a stabilization or reduction in the growth and/or formation of a tumor. In some embodiments, such terms refer to the eradication, removal, or control of primary, regional, or metastatic cancer (e.g., the minimization or delay of the spread of cancer). In some embodiments, such terms refer to a reduction in mortality and/or an increase in survival rate of a patient population. In further embodiments, such terms refer to an increase in the response rate, the durability of response, or number of patients who respond or are in remission. In some embodiments, such terms refer to a decrease in hospitalization rate of a patient population and/or a decrease in hospitalization length for a patient population.

Cortisol

The estimated daily cortisol production rate in normal subjects varies between 4-15 mg/m$^2$ per day or, according to more recent studies between 9 and 11 mg/m$^2$ per day. In order to describe the 24-hour variation in serum cortisol levels adequately, the day may be divided into, for example, four phases. Phase 1 is a 6-hours period of minimal secretory activity 4 h before and 2 h after onset of sleep. Phase 2 refers to the 3rd to 5th hours of sleep when there is a preliminary nocturnal secretory episode. Phase 3 is a 4-hour main secretory phase during the last 3 h of sleep and the first hour after wakening. Phase 4 is an 11-hour phase of intermittent secretory activity when there is a slow decline in serum levels of cortisol.

In a study by Mah et al. (Clinical Endocrinology (2004) 61, 367-375) the circadian rhythm of serum cortisol of normal subjects is described. Peak levels of about 400-800 mmol/l, about 150-300 mmol/l and about 150 mmol/l are observed at about 6 am, 2 pm and 9 pm, respectively, and the lowest level is about midnight. In this study it is observed that the endogenous cortisol levels reach their highest levels within 30 minutes after wake-up. In order to mimic the circadian rhythm, Mah et al. recommend a thrice-daily treatment regimen of hydrocortisone, the first dose taken in the fasted state and delaying the breakfast 1-3 hours and the other two doses taken 15-60 min before food. A trice-daily regimen is also recommended in a recent review by Czock et al. (Clin. Pharmacokinet (2005) 44, 61-98) due to the short half-life of hydrocortisone, and for prednisolone a twice-daily regimen is preferred over a once-daily regimen.

Cortisol Test

The absence of rapid response and inexpensive testing for cortisol has, heretofore, prevented the linking of GCR antagonists (e.g., ORG 34517) to a cortisol pre-test for entry into clinical trials for GCR antagonists and will inhibit the ability to select the patients most likely to receive the benefit of treatment with the compounds when available for clinical use. The invention provides the pairing of an affordable, real-time cortisol test (e.g., PopTest Cortisol) which will enable the successful completion of clinical trials for this class of drugs as well as form the basis for their future, anticipated therapeutic use(s).

Conditions that may be treated using, for example, a linked salivary cortisol quantification test and GCR antagonist (e.g., ORG 34517) system include, but are not limited to the following:

Major Depressive Disorder (MDD).

MDD is a psychiatric disorder which has a lifetime prevalence of around 8%. One of the most consistent findings in psychiatry is that patients with major depression present with alterations in the hypothalamic-pituitary-adrenal (HPA) axis. A significant percentage of depressed patients exhibit hypersecretion cortisol, as manifested by elevated plasma, cerebrospinal fluid, and salivary concentrations of cortisol and increased urinary free cortisol. In addition, many depressed patients exhibit a clear inability to switch off endogenous cortisol release following exogenous challenge with the potent synthetic glucocorticoid dexamethasone (the so-called dexamethasone non-suppressors) (Gold P. W., et al., Clinical and biochemical manifestations of depression: relation to neurobiology of stress. New England J. Med. 319, 413-420, 1988). This 'sub-group' of severely compromised patients are most often the ones in whom depression becomes a life-threatening illness that warrants hospitalization.

Other abnormalities of the HPA axis found in depressed patients are increased cortisol response to corticotrophin, a blunted corticotrophin response to CRH (corticotrophin releasing hormone), and adrenal and pituitary enlargement (for a review see Holsboer, F. and Barden, N.: Endocrine Reviews 1996, 17, 187-205). These observations have been interpreted to suggest a causal relationship between disturbed functioning of the HPA axis and the pathology of depression (Murphy, B. E. P. J. of Steroid Biochem. and Mol. Biol. 1991, 38, 537-559). Therapeutic efficacy of classical antidepressants has been shown to be preceded by or to coincide with restoration of the disturbed HPA axis in depression (Holsboer and Barden, 1996, supra). It has been postulated that any intervention which can restore this HPA dysfunction may have antidepressant potential.

One type of such intervention, studies of which support the impression that HPA-axis functioning and high circulating cortisol is a major instigator of major depression is the administration of glucocorticoid synthesis inhibitors, as has been shown in patients suffering from Cushing's Syndrome, which is a condition in which high cortisol levels are reported as a result of adrenal gland malfunction (due to a pituitary tumour or a secondary tumour, both producing the cortisol secretagogue ACTH). The depressive symptoms associated with Cushing's disappear relatively quickly with the return of cortisol levels to normal. Such treatment may involve removal of the offending tumour or treatment with cortisol synthesis inhibitors such as metyrapone, ketoconozole, or aminoglutethimide (Murphy, B. E. P., Steroids and Depression. J. Steroid Biochem & Mol. Biol. 38, 537-558, 1991). Similarly, relatively recent clinical trials have demonstrated that cortisol synthesis inhibitors can be used to ameliorate depressive symptoms in severe, treatment-resistant non-Cushing depressives (Murphy, B. E. P., Can. J. Psych. 43, 279-286, 1998; see also U.S. Pat. No. 4,814,333 (Ravaris, C. L.)).

Another type of intervention is the use of direct GCR antagonists, which have much more specific pharmacological effects as compared to synthesis inhibitors and which may help restore HPA activity. Small scale pilot clinical studies have been conducted in order to study the antidepressant activity of the non-selective glucocorticoid receptor antagonist RU 486 (mifepristone; Murphy, B. E. P. et al. J. Psychiat. Neurosc. 18, 209-213, 1993). More recently (Nemeroff, C., Remeron Scientific Expert Meeting, Budapest, Mar. 29-Apr. 1, 2001) it was demonstrated in a Phase IIB continuation of this study, that both the number of responders as well as the efficacy of the psychosis treatment increased with increasing daily dose of mifepristone as measured by the change in Brief Psychiatric Rating Scale (50 mg—33% change; 600 mg—40% change and 1200 mg—52% change). These data indicate that a higher dose of glucocorticoid receptor antagonist is correlated with a higher clinical efficacy.

Non-response to standard treatments, however, reach levels as high as 50%. (Connolly K R, Drugs. 2011; 71: 43-64.) Frequently, extra interventions are necessary to get patients to achieve remission. Various augmentation and combination strategies have been described in the literature for difficult to treat major MMD patients.

Use of an HPA-axis modulating drug in these patients has not been studied in spite of the fact that there is clear evidence that at least a sub-group of MDD patients have significant HPA-axis dysfunction, as noted above. Biological symptoms, indicative of excessive activity of the HPA-axis, have been reported with great consistency. In parallel, there is a body of evidence suggesting that there is an association between HPA-axis functioning and treatment response, where high HPA-axis activation at baseline, or post-treatment, is associated with a poorer response to SSRI treatment or a higher relapse risk.

Preclinical studies indicate that HPA-axis dysfunction of the type seen in affective disorders can attenuate the neurochemical effects of a selective serotonin re-uptake inhibitor (SSRI) antidepressant. Conversely, in animals with normal HPA axis function, co-administration of GR antagonists augmented the neurochemical effects of an SSRI. These data provide a mechanistic underpinning of the GR antagonist augmentation strategy, and moreover indicate that the strategy may prove efficacious in patients both with and without HPA axis dysfunction.

Small scale pilot clinical studies were conducted in order to study the antidepressant activity of the non-selective glucocorticoid receptor antagonist RU 486 (mifepristone; Murphy, B. E. P. et al. J. Psychiat. Neurosc. 18, 209-213, 1993). A double blind, 4 week, paroxetine controlled study of ORG 34517 in depressed patients was carried out. Paroxetine is a selective serotonin re-uptake inhibitor which is recognized as an effective antidepressant for major depression. Patients were selected which had a primary depressive disorder fulfilling the diagnostic criteria of a MDD as defined by the DSM-IV for recurrent (296.3) episodes, and who had a severity of depression which resulted in a total score of at least 22 on the HAMD-21 (Hamilton Rating Scale for Depression; see Hamilton, M. "A rating scale for depression." J. Neurol. Neurosurg. Psychiat. 1960, 23, 56-62) scale at baseline. Patients had an episode of depression which had lasted at least 2 weeks before baseline.

In this study, patients were randomly allocated to one of three treatment groups. Group I patients (50 patients) received 2 capsules with 75 mg of ORG 34517 and one placebo (total daily dose 150 mg) for the first 2 weeks and 2 capsules with 75 mg ORG 34517 and 1 capsule with 150 mg (total daily dose 300 mg) the next 2 weeks; Group II patients (46 patients) received 3 capsules with 150 mg ORG 34517 (total daily dose 450 mg) in the first 2 weeks and 4 capsules of ORG 34517 (total daily dose 600 mg) in the next 2 weeks; Group III patients (44 patients) received 2 capsules with 10 mg paroxetine and one placebo capsule (total daily dose 20 mg) for the first 2 weeks, followed by 2 capsules of 10 mg and one capsule of 20 mg paroxetine (total daily dose 40 mg) in the next 2 weeks. Medication was administered orally in the morning. Efficacy assessment was done on days 4, 7, 10, 14, 21, 28 and 35 by using the 21-item HAMD scale.

Thus, GCR antagonist therapy could prove a useful mechanism for treatment of selected individuals who fail to respond to current anti-depressant therapies such as SSRIs, providing a way to enhance responsiveness or as an alternate means of achieving a maintained euthymia.

Psychotic Depression.

Psychotic major depression has long been recognized as a distinct psychiatric illness, having both psychotic and depressive components in a differential diagnosis. Psychotic major depression is very common. It has been estimated that twenty five percent of depressed patients admitted to the hospital have psychotic major depression (Coryell (1984) J. Nerv. Ment. Dis. 172:521). Like major depression, psychotic depression is often also a result of high circulating cortisol levels. Various evidence supports this concept. Psychosis has been associated with Cushing's syndrome (Gerson (1985) Can. J. Psychiatry 30:223-224; Saad (1984) Am. J. Med. 76:759-766). A GR antagonist has been used to treat acute psychiatric disturbances secondary to Cushing's syndrome. One study showed that a relatively high dose of such a GR antagonist (400 to 800 mg per day) was useful in rapidly reversing acute psychosis in patients with severe Cushing's' Syndrome due to adrenal cancers and ectopic secretion of ACTH from lung cancer (Van der Lely (1991) Ann. Intern. Med. 114:143; Van der Lely (1993) Pharmacy World & Science 15:89-90; Sartor (1996) supra). Relatively high dose mifepristone, in the range of 8-12 mg/kg/day, over a relatively short period of time (4 days), was also shown to be effective in the treatment of psychosis associated with psychotic major depression (International Patent Application WO 99/17779; Schatzberg and Belanoff).

Surgery-Associated Immune Suppression in the Elderly.

In healthy, young to middle aged subjects suffering from stress, there is a physiological balance between pro-inflammatory and anti-inflammatory mediators. In the elderly, the immune response is blunted as a result of the decline in several components of the immune system (immune senescence) and a shifting to a chronic pro-inflammatory status (the so-called "inflammaging" effect (Butcher and Lord, (2004) Aging Cell, pp. 151-160). As production of cortisol remains reasonably constant with age, whereas summed levels of DHEA and DHEAS decrease gradually from the third decade, reaching 10-20% of their maximum by the eighth decade, Butcher and Lord (2004, supra) propose a model for age and stress, in which the age-related increase in the ratio of cortisol to DHEAS, combined with an elevated cortisol release during stress, leads to a significant reduction of immunity in aging subjects. This is proposed to explain that aging subjects are far more prone to infections under conditions of stress. (Butcher and Lord (2004, supra); Butcher et al. (2005, Aging Cell 5, pp. 319-324).

The present invention relates to the use of a GCR antagonist for the prevention or treatment of infections or infectious conditions, in an aging patient, such as a human subject. The beneficial effects of said GCR antagonists may be explained on the basis of their correcting influence on the cortisol/DHEA(S) ratio. It is believed that the effect in selected subjects, found to have high circulating cortisol by a saliva test as provided for by this invention, can be explained by the unbalanced immunosuppressive role of the increased cortisol/DHEAS ratio in the aged group in comparison to the balanced influence of cortisol and DHEAS on the immune system in normal subjects.

The meaning of the term 'aging subject' or 'aged subject' will be well understood in the context of the use according to this invention. Although it is not linked to an exact lower age limit this general notion refers in the human situation usually to a person of at least 55 years old, but it is more clear with a lowest age limit set at 60, 65, 70 or 75 years.

In the context of the invention, the infection or infectious condition can be caused by any of several agents, e.g., by bacteria, by viruses or by fungi. Also in the context of the present invention, the expression "infectious conditions" means silent or subclinical infections as well as conditions not resulting in a manifest infectious disease, but in which at least one parameter associated with an infectious disease, such as the white blood (e.g., neutrophil, basophil or eosinophil) cell counts or the level of some antibodies or some cytokines is higher than normal. Normal values are known to the expert and may be found in standard medical manuals.

Particular uses according to the invention relate to aging subjects suffering from an infection or an infectious condition concomitant to stress resulting from a trauma. The invention particularly relates to uses wherein the subject suffers from the consequences of a bone fracture and/or bone surgery, either for such injury or for joint replacement for osteoarthritis or rheumatoid arthritis. The invention also relates to uses wherein the subject suffers from an infection or an infectious condition concomitant to psychological stress, particularly acute emotional stress.

Post Traumatic Stress Disorder (PTSD).

PTSD is a severe anxiety disorder that can develop after exposure to any event that results in psychological trauma. This event may involve the threat of death to oneself or to someone else, or to one's own or someone else's physical, sexual, or psychological integrity, overwhelming the individual's ability to cope. As an effect of psychological trauma, PTSD is less frequent and more enduring than the more commonly seen acute stress response. Diagnostic symptoms for PTSD include re-experiencing the original trauma(s) through flashbacks or nightmares, avoidance of stimuli associated with the trauma, and increased arousal, such as difficulty falling or staying asleep, anger, and hyper-vigilance. Formal diagnostic criteria (both DSM-IV-TR and ICD-9) require that the symptoms last more than one month and cause significant impairment in social, occupational, or other important areas of functioning. (Diagnostic and statistical manual of mental disorders: DSM-IV. American Psychiatric Association. 1994. Washington, D.C.: American Psychiatric Association.)

PTSD displays biochemical changes in the brain and body that differ from other psychiatric disorders such as major depression. Abundant evidence suggests derangement of HPA-axis physiology in individuals diagnosed with PTSD, though the nature of the derangements is variable: some have low cortisol, some have normal levels, others have high levels of cortisol and for some, levels may be normal, but circadian rhythm is lost. It is postulated that these reflect different baseline mechanisms, but that when cortisol is high, either in a sustained way through the day or by loss of circadian rhythm with elevated night time levels, it is likely to be an important component of the clinical symptomatology (Lindley S E, et al. Basal and dexamethasone suppressed salivary cortisol concentrations in a community sample of patients with posttraumatic stress disorder. Biol. Psychiatry 2004; 55: 940-5). In such patients, determined by salivary cortisol testing, administration of a GCR antagonist is expected to be therapeutic or beneficial for the symptoms of PTSD.

Prevention of Weight Gain in Patients Using Anti-Psychotic and Anti-Depressant Medications.

Anti-psychotic and some anti-depressant medications (e.g., SSRIs) are amongst the most important tools for treating psychiatric conditions of all kinds. However, management of patients on who take many of these medications for chronic, long term disease is made difficult by their significant side effect profiles. One of the most important of these is weight gain and the attendant metabolic syndrome that follows. For example, it is estimated that 40-80% of patients who are under chronic anti-psychotic administration experience substantial weight gain, often exceeding 20% or more over their ideal body weights (Umbricht et al. J Clin. Psychiatry 1994; 55: 157-160; Khan A Y, et al. J Psychiatr Pract. 2010; 16: 289-96; Pramyothin P, Khaodhiar L. Curr Opin Endocrinol Diabetes Obes. 2010; 17: 460-6.; Rummel-Kluge C et al. Schizophr Res. 2010; 123: 225-33). Such weight gain is one of the most common causes of poor compliance with anti-psychotic and anti-depressant regimens and, therefore, of long term failure of therapy. Furthermore, anti-psychotic medications specifically are commonly associated with development of insulin resistance and metabolic syndrome (with development of type 2 diabetes mellitus and hyper/dyslipidemia states) and the potentially and significantly increased risks for cardiovascular disease; these conditions are of tremendous medical consequence for patients who are thereby caught in a "can't live with them, can't live without them" treatment scenario. While weight gain is potentially seen with all anti-psychotic medications, they are particularly common and tend to more severe with the newer or "atypical" AP drugs (Allison et al. Am J Psychiatry 1999; 156:1686-1696; Rummel-Kluge C et al. Schizophr Res. 2010; 123: 225-33).

Elevations in cortisol are associated with changes in body fat and insulin resistance. Several years ago, in a proof of principle clinical experiment, it was reported that one GCR antagonist (mifepristone) was a highly effective treatment for multiple medical complications in a patient with Cushing's disease whose illness had not responded to surgery and radiation, including reversal of insulin dependent diabetes: the patient was able to stop insulin within a month (Chu et al., J. Clin. Endocrinol. Metab. 2001; 86, 3568-3573.). These data suggest that a GCR antagonist could be useful for blocking and reversing the insulin resistance and weight changes seen in some patients treated with atypical antipsychotic agents. To this end, this compound was tested in rats who had olanzapine-induced weight gain and increases in abdominal fat; reversal of weight gain was seen and reduction of abdominal fat was obtained (Beebe et al. Behav. Brain Res. 2006; 171, 225-229). A clinical trial with this compound then confirmed this benefit in humans with a 2 week study of 600 mg/day of mifepristone that reduced olanzapine-induced weight gain in 57 non-overweight healthy males with Body Mass Indices less than 25 (Gross et al., Adv Ther. 2009; 26: 959-69.). Thus, GCR antagonist therapy could prove a useful mechanism to target in treating psychotic patients with atypical antipsychotic agents.

Cushing's Syndrome.

Cushing's Syndrome is a set of conditions in which high levels of circulating cortisol or other GCR agonists cause a set of seriously debilitating and sometimes life threatening signs and symptoms including, but not limited to, psychiatric disturbances (e.g. anxiety, depression, psychosis), immunosuppression, insulin resistance and metabolic syndrome, skin conditions, hypertension and osteoporosis. Endogenous cortisol may be produced by ACTH-secreting, benign or malignant tumors of the pituitary gland ("Cushing's Disease") or of the adrenal cortex. These are rare conditions and therefore Cushing's Syndrome is considered an "orphan disease."

A proof of concept trial using RU486 to treat patients with tumor-related Cushing's Syndrome demonstrated efficacy in remitting symptoms such as glucose metabolic abnormalities (i.e., glucose intolerance; (group 1) and hypertension (group 2). Statistically significant improvement was achieved for both groups: with 60% responding in the glucose intolerant group and 43% in the hypertensive group (Corcept Therapeutics Press Release Dec. 22, 2010). Thus, GCR antagonist therapy can be expected to provide clinical benefits for patients with Cushing's Syndrome administered prior to tumor surgery to improve surgical outcomes and/or post-surgery to mitigate symptoms in patients for whom surgical cure is not achievable.

In addition, GCR antagonist therapy can be expected to provide clinical benefits for patients, for example, in hospitals, nursing homes, nurseries, daycares, schools, work environments, public transportation, healthcare settings, psychiatric institutions, and long-term nursing facilities Diagnostic Systems and Kits A diagnostic kit may comprise some or all of the following components: 1) one or more standards comprised of one or more of the biomarker(s) of the invention, such as cortisol; 2) a ligand, such as an antibody or a plurality of antibodies, that are specific for the biomarker(s) that are to be assayed for using the kit; 3) written instructions; 4) diluents for samples and the standards; 5) a wash buffer; 6) color reagents; 7) stop solution; and 8) a ligand carrier, such as an antibody carrier, for example, a lateral flow device, or a microplate with bound antibody, or polystyrene beads.

An example of such a kit is a quantitative ELISA (enzyme-linked immunosorbent assay) that determines the concentration or concentrations of the biomarker or biomarker(s) in accordance with methods embodied by the invention. The principle of the assay is to use the quantitative sandwich enzyme immunoassay technique wherein a monoclonal or polyclonal antibody selective for a biomarker is pre-coated onto a carrier such as a microplate into its wells. The standards and sample are then pipetted into the wells and any of the biomarker that is present is bound to this immobilized antibody. Next, the wells are washed with washing buffer, and an enzyme-linked monoclonal or polyclonal antibody that is specific for the biomarker is added to the wells. Washing is again performed, then a substrate solution is added to the wells. Color subsequently develops in proportion to the amount of polypeptide of the invention that is bound in the first step. The color development is stopped using a stop solution, and the intensity of the color is measured by a microplate reader.

The methods of the invention may be carried out using, for example, a lateral flow assay. Such lateral flow assays have the potential to be a cost-effective, fast, simple, and sensitive method, for instance for on-site screening assays. The lateral flow assay comprises a carrier that allows a lateral flow to occur wherein either the sample or the detection reagent is displaced form one location on the carrier to another. There are many formats of lateral flow assays suitable for use in a method embodied by the invention, and the skilled person will readily know how to select and optimize a particular format. An example of a lateral flow test strip of the invention comprises, for example, the following components:

1. Sample pad—an absorbent pad onto which the test sample is applied.

2. Conjugate or reagent pad—this contains antibodies specific to the target analyte conjugated to colored particles (usually colloidal gold particles, or latex microspheres).

3. Reaction membrane—typically a hydrophobic nitrocellulose or cellulose acetate membrane onto which anti-target analyte antibodies are immobilized in a line across the membrane as a capture zone or test line (a control zone may also be present, containing antibodies specific for the conjugate antibodies).

4. Wick or waste reservoir—a further absorbent pad designed to draw the sample across the reaction membrane by capillary action and collect it.

Double Antibody Sandwich Assays—

In this format the sample migrates from the sample pad through the conjugate pad where any target analyte present will bind to the conjugate. The sample then continues to migrate across the membrane until it reaches the capture zone where the target/conjugate complex will bind to the immobilized antibodies producing a visible line on the membrane. The sample then migrates further along the strip until it reaches the control zone, where excess conjugate will bind and produce a second visible line on the membrane. This control line indicates that the sample has migrated across the membrane as intended. Two clear lines on the membrane is a positive result. A single line in the control zone is a negative result. Double antibody sandwich assays are most suitable for larger analytes, such as bacterial pathogens and viruses, with multiple antigenic sites. Competitive assays are primarily used for testing small molecules and differ from the double antibody sandwich format in that the conjugate pad contains antibodies that are already bound to the target analyte, or to an analogue of it. If the target analyte is present in the sample it will therefore not bind with the conjugate and will remain unlabelled. As the sample migrates along the membrane and reaches the capture zone, an excess of unlabelled analyte will bind to the immobilized antibodies and block the capture of the conjugate, so that no visible line is produced. The unbound conjugate will then bind to the antibodies in the control zone producing a visible control line. A single control line on the membrane is a positive result. Two visible lines in the capture and control zones is a negative result. However, if an excess of unlabelled target analyte is not present, a weak line may be produced in the capture zone, indicating an inconclusive result. Competitive assays are most suitable for testing for small molecules, such as mycotoxins, unable to bind to more than one antibody simultaneously. There are a number of variations on lateral flow technology. The capture zone on the membrane may contain immobilized antigens or enzymes—depending on the target analyte—rather than antibodies. It is also possible to apply multiple capture zones to create a multiplex test. For example, commercial test strips able to detect both EHEC Shiga toxins ST1 and ST2 separately in the same sample have been developed. Lateral flow immunoassays are simple to use by untrained operators and generally produce a result within 15 minutes. They are very stable and robust, have a long shelf life and do not usually require refrigeration. They are also relatively inexpensive to produce. These features make them ideal for use at the point-of-care and for testing samples in the field, as well as in the laboratory. However, their sensitivity is limited without additional concentration or culture procedures.

Quantitative Tests—

While most lateral flow immunoassays are only capable of providing a qualitative result, it is possible to obtain some degree of quantification by measuring the amount of conjugate bound to the capture zone. This can be done using a dedicated reader to measure the intensity of the colored test line. For example, the Neogen Corporation has developed the Accuscan™ lateral flow reader for use with its range of Reveal® assay kits and Charm Sciences also supplies a reader for its Rosa® range of mycotoxin test strips. More sophisticated techniques, such as fluorescent dye labeled conjugates, have also been developed to improve the quantitative potential of lateral flow assays. Applications in the 20 years since the first lateral flow test was launched have expanded to include a huge range of different tests that have been developed based on the same technology. The first commercially available kits were aimed at the clinical diagnostics field, but there are now products with applications in almost every branch of microbiology. Clinical microbiology—lateral flow tests have been developed for bacterial pathogens, respiratory and enteric viruses, intestinal parasites and bacterial toxins. Many of the lateral flow immunoassay products designed for the clinical sector were intended to be used at the point-of-care for direct testing of fecal, blood and urine samples and nose and throat swabs, where the simple operation and speed of the tests is key to their use outside of the laboratory. However, the same test strips may also be useful as a quick confirmatory test following laboratory culture of clinical samples. Food and agricultural microbiology—test strips are available for food borne bacterial pathogens, bacterial and fungal toxins. In the food microbiology sector, the main applications are more likely to be in the laboratory, although there are field test kits for mycotoxins in grain samples. Testing for food borne bacterial pathogens generally involves at least one enrichment stage before the assay strip is used to confirm the presence or absence of the pathogen. Some manufacturers, such as Dupont®, have developed enrichment media and methods specifically designed for use with lateral flow test strips. Test strips may also be useful for rapid confirmation of the identity of bacterial isolates from conventional microbiological testing.

A diagnostic system in kit form of the present invention includes, for example, in an amount sufficient for at least one assay, a polypeptide, antibody composition or monoclonal antibody composition of the present invention, as a packaged reagent. Instructions for use of the packaged reagent are also typically included.

A diagnostic system in kit form of the present invention may include, for example, a means for detecting the presence of a biological substance in a test sample, comprising for example, a lollipop-like apparatus including a stem integrated with the base and a head integrated with the stem, for collecting a test sample consisting of, for example, saliva, or a bodily fluid sample from a subject. The stem head may include a receptor of a sponge like carrier to ensure a high void volume to absorb sufficient saliva, or bodily fluid sample. See U.S. Pat. No. 7,993,283, incorporated by reference herein in its entirety.

A diagnostic system in kit form of the present invention may include, for example, a means for combining the test sample with a buffering system (Reagent 1) containing viscosity controllers and stabilizers into a reaction vessel and mixing the solution. A diagnostic system in kit form of the present invention may include, for example, a means for reading the a parameter of the reaction vessel with sample and buffer, and further means for combining the test sample and buffer mixture with a fluorescence-labeled ligand (Reagent 2) to said biological substance in the reaction vessel, mixing the solution to produce an assay solution. Furthermore, Reagent 2 may be delivered to the reaction vessel without further dilution volume of the assay solution.

As used herein, the term "package" refers to a solid matrix or material such as glass, plastic, paper, foil and the like capable of holding within fixed limits a polypeptide, antibody composition or monoclonal antibody composition of the present invention. Thus, for example, a package can be a glass vial used to contain milligram quantities of a contemplated polypeptide or it can be a microliter plate well to which microgram quantities of a contemplated polypeptide have been operatively affixed, i.e., linked so as to be capable of being immunologically bound by an antibody.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalene-sulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in Antibody As a Tool, Marchalonis, et al., eds., John Wiley & Sons, Ltd., pp. 189-231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such $^{111}$indium or $^{3}H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3-46 (1981). The techniques of protein conjugation or coupling through activated functional groups are particularly applicable. See, for example, Aurameas, et al., Scand. J. Immunol., Vol. 8 Suppl. 7:7-23 (1978), Rodwell et al., Biotech., 3:889-894 (1984), and U.S. Pat. No. 4,493,795, which are all incorporated herein by reference.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, S. aureus protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect, for example, the presence or quantity of cortisol in a body fluid sample such as serum, plasma, or urine, etc. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of Basic and Clinical Immunology by D. P. Sites et al., published by Lange Medical Publications of Los Altos, Calif. in 1982 and in U.S. Pat. No. 3,654,090; U.S. Pat. No. 3,850,752; and U.S. Pat. No. 4,016,043, which are all incorporated herein by reference.

Thus, for example, a polypeptide, antibody molecule composition or monoclonal antibody molecule composition of the present invention can be affixed to a solid matrix to form a solid support that comprises a package in the subject diagnostic systems. The reagent is typically affixed to the solid matrix by adsorption from an aqueous medium although other modes of affixation, well known to those skilled in the art, can be used.

Useful solid matrices are also well known in the art. Such materials are water insoluble and include cross-linked dextran; agarose; beads of polystyrene beads about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like. In one embodiment a diagnostic system of the present invention is useful for assaying for the presence of, for example, cortisol. Such a system comprises, in kit form, a package containing an antibody to, for example, cortisol.

"Sample" refers to, for example, essentially any source from which materials of interest to be analyzed (e.g., ligands and antiligands, such as antibodies and antigens, and nucleic acids and their complements) can be obtained. A sample may be acquired from essentially any organism, including animals and plants, as well as cell cultures, recombinant cells and cell components. Samples can be from a biological tissue, fluid or specimen and may be obtained from a diseased or healthy organism. Samples may include, but are not limited to, saliva, sputum, amniotic fluid, blood, blood cells (e.g., white cells), urine, semen, peritoneal fluid, pleural fluid, tissue or fine needle biopsy samples, and tissue homogenates. Samples may also include sections of tissues such as frozen sections taken for histological purposes. Typically, samples are taken from a human. However, samples can be obtained from other mammals also, including by way of example and not limitation, dogs, cats, sheep, cattle, and pigs. The sample may be pretreated as necessary by dilution in an appropriate buffer solution or concentrated, if desired. Any of a number of standard aqueous buffer solutions, employing one of a variety of buffers, such as phosphate, Tris, or the like, preferably at physiological pH can be used.

Biological samples can be derived from patients using well known techniques such as venipuncture, lumbar puncture, fluid sample such as saliva or urine, or tissue biopsy and the like. When the biological material is derived from non-humans, such as commercially relevant livestock, blood and tissue samples are conveniently obtained from livestock processing plants. Alternatively, a biological sample may be obtained from a cell or blood bank where tissue and/or blood are stored, or from an in vitro source, such as a culture of cells. Techniques for establishing a culture of cells for use as a source for biological materials are well known to those of skill in the art.

In one embodiment the sample is selected from or is derived from, for example, microbial products or biological products.

Although the above described example relates to the antigens relating to disease, the immunoassay apparatus could be used, for example, as an allergy test kit, as a test kit for drugs of abuse or for analyzing non-human derived samples e.g. bovine, porcine, and veterinary tests.

Specific reagents used in the assay device will be selected so as to ensure that the particular target analyte is detected as is well known in the art. The target analyte may be any analyte for example a chemical reagent which may be organic or inorganic, and which optionally comprises a hapten, a protein, a polypeptide, a microorganism or a nucleic acid sequence.

In particular, the analyte is a hormone such as a fertility hormone like progesterone or a stress hormone such as cortisol. However, there is a wide range of applications of these types of tests across the entire field of diagnostics and analysis. Detection of marker proteins or hormones can be diagnostic of certain disease conditions in humans or animals, and the presence of drugs or drug residues may also be required to be detected, for example, in animal husbandry, forensic medicine or in the testing for banned or prohibited drug substances.

Alternatively, the analyte is a chemical reagent, for instance a small molecule, which suitably comprises a hapten. Small molecules will generally comprise a single recognizable binding site. Typically they will have a molecular weight of less than 1 kDa.

Where the assay utilizes a labelled binding partner for the analyte and the analyte is a chemical reagent, the binding partner may comprise any other reagent which reacts with or otherwise becomes associated with the chemical reagent, either because it forms covalent or ionic bonds with the reagent, or by the formation of other interactions, such as hydrogen bonding or Van der Waals interactions. For example, where the chemical reagent is an acid, the binding partner may comprise an alcohol or an amine that forms an ester or amide with the acid under the sorts of conditions found in the test. Alternatively the binding partner may comprise a base that forms a salt with the acid. Conversely, where the binding partner may comprise the acid part of the reactive pair.

Where the analyte is or comprises a hapten or a protein antigen, the binding partner may comprise an antibody or a binding fragment thereof, which may be monoclonal, polyclonal or recombinant, but preferably is monoclonal. Where the analyte is a hormone or enzyme, the labelled binding partner may comprise a labelled receptor for the analyte. However, where the analyte is itself an immunoglobulin, and in particular, an antibody, the labelled binding partner may also comprise for instance, an antigen or recombinant antigen, as well as anti-antibody immunoglobulin such as antisera.

Antibodies or binding fragments to small molecules such as haptens, are generated by attaching the molecule to an immunogenic reagent and administering this to an animal such as a mouse or rabbit. Antibodies are then harvested from the animal in the usual way. Monoclonal antibodies are obtained by fusing spleen cells to hybridoma cells, and selecting those which bind the hapten, using routine procedures.

For example, where the analyte is a biologically active material such as an active agrochemical as discussed above, specific reagents used in the assay device will be selected so as to ensure that the particular target biologically active material is detected as is well known in the art. The biologically active material may be any active chemical such as an agrochemical, for example a chemical reagent which may be organic or inorganic, and which optionally comprises a hapten, a protein, a polypeptide, a microorganism or a nucleic acid sequence. Most preferably the biologically active material is a chemical reagent, for instance a small molecule, which suitably comprises a hapten. Small molecules will generally have a single antibody binding site. Typically they will have a molecular weight of less that 1 kDa.

Antibodies or binding fragments to small molecules such as haptens, are generated by attaching the molecule to an immunogenic reagent and administering this to an animal such as a mouse or rabbit. Antibodies are then harvested from the animal in the usual way. Monoclonal antibodies are obtained by fusing spleen cells to hybridoma cells, and selecting those which bind the hapten, using routine procedures.

Microarrays

The method of the invention is particularly useful in combination with the analysis of gene expression profiles. In some embodiments, a gene expression profile, such as a collection of transcription rates of a number of genes, is converted to a projected gene expression profile. The projected gene expression profile is a collection of expression values. The conversion is achieved, in some embodiments, by averaging the transcription rate of the genes. In some other embodiments, other linear projection processes may be used.

Microarrays may be prepared and analyzed using methods known in the art. Oligonucleotides may be used as either probes or targets in a microarray. The microarray can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc. Natd. Acad. Sci. 93:10614-10619; Baldeschweiler et al. (1995) PCT application WO95/251116; Shalon et al. (1995) PCT application WO95/35505; Heller et al. (1997) Proc. Natl. Acad. Sci. 94:2150-2155; and Heller et al. (1997); U.S. Pat. No. 5,605,662.) Hybridization probes are also useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome DNA libraries.

Using the methods of the invention a skilled artisan can readily select and prepare probes for a microarray wherein the microarray contains specific individual probes for less than all the genes in the genome and less than all the genes in the genome. In such embodiments, the microarray contains one or two or more individual probes, each of which hybridizes to an expression product (e.g., mRNA, or cDNA or cRNA derived therefrom) for a desired number of genes. Thus, for example, changes in the expression of all or most of the genes in the entire genome of a cell or organism can thereby be monitored by use of a surrogate and on a single microarray by measuring expression of the group of genes that are representative of all or most of the genes of the genome. Such microarrays can be prepared using the selected probes and are therefore part of the present invention.

Glucocorticoid Receptor

The glucocorticoid receptor is widely distributed and expressed in many cultured cell lines, and the control of gene expression by glucocorticoids, therefore, has been widely studied as a model for transcriptional regulation. A number of glucocorticoid-responsive transcription units, including mouse mammary tumor virus (MMTV) (Ringold, et al., 1975; Parks, et al., 1974), mouse and human metallothionein (Eager, et al., 1981; Karin, et al., 1980), rat alpha$_2$M-globulin (Kurtz, et al., 1977) and rat and human growth hormone (Spindler, et al., 1982; Evans, et al., 1982; Robins, et al., 1982) genes have been identified. DNA sequences mediating transcriptional stimulation of several of these genes have been localized. For MMTV, these sequences are discrete genomic regions upstream of the transcriptional start site which appear to exert their actions independently of orientation and position (Chandler, et al., 1983; Ostrowski, et al., 1984). The steroid/receptor complex appears to bind to these regulatory sequences and purified receptor has been used to define the specific binding sites (Govinda, et al., 1982; Scheidereit, et al., 1983; Pfahl, 1982; Payvar, et al., 1983). The ability of the glucocorticoid-responsive element (GRE) to alter its position and orientation yet still maintain promoter inducibility suggests that it resembles the class of cis-acting regulatory sequences termed enhancers (Chandler, et al., 1983). First discovered in viruses and subsequently in cellular genes, these sequences are necessary for efficient transcription in vivo (Laimonis, et al., 1982; Benoist, et al., 1981; Baerji, et al., 1983). It has been suggested that enhancers are recognized by trans-acting factors that mediate regulatory effects by tissue-specific transcriptional control. Although the enhancer factors have not been well characterized, the glucocorticoid receptor may serve as a paradigm for these putative gene activator proteins.

It is generally accepted that the unliganded glucocorticoid receptor (GR) resides in the cytoplasm, and that hormone activation leads both to nuclear accumulation and gene activation. (Gasc, J.-M. & Baulieu, E. E. (1987) in Steroid Hormone Receptors: Their Intracellular Localisation, ed. Clark, C. R. (Ellis Horwood Ltd., Chichester, England), pp. 233-250; Beato, M. (1989) Cell 56, 335-344; Carson-Jurica, M. A., Schrader, W. T. & O'Malley, B. W. (1990) Endocr. Rev. 11, 201-220; Gronemeyer, H. (1993) in Steroid Hormone Action, ed. Parker, M. G. (Oxford University Press, New York), pp. 94-117; Tsai, M. J. & O'Malley, B. W. (1994) Annu. Rev. Biochem. 63, 451-486; Akner, G., Wikstrom, A. C. & Gustafsson, J. A. (1995) J. Steroid Biochem. Mol. Biol. 52, 1-16), and references therein. However, the mechanisms involved in nuclear translocation and targeting of steroid receptors to regulatory sites in chromatin have been poorly understood. It has previously been difficult to discriminate between the ability of a given receptor mutant, or a given receptor/ligand combination, to participate in the separate processes of receptor activation, nuclear translocation, sequence-specific binding, and promoter activation.

The glucocorticoid receptor (GR) is expressed in a subset of both ERalpha-positive and -negative human breast cancers as well as in some ovarian cancers. In vitro and in vivo experiments suggest that activation of the GR in ER-negative pre-malignant breast epithelial and cancer cells initiates cell survival pathways under stress conditions that normally induce significant cell death (e.g. chemotherapy, radiation, growth factor deprivation).

The glucocorticoid receptor (GR) is present in glucocorticoid responsive cells where it resides in the cytosol in an inactive state until it is stimulated by an agonist. Upon stimulation the glucocorticoid receptor translocates to the cell nucleus where it specifically interacts with DNA and/or protein(s) and regulates transcription in a glucocorticoid responsive manner. Two examples of proteins that interact with the glucocorticoid receptor are the transcription factors, API and NFκ-B. Such interactions result in inhibition of API- and NFκ-B-mediated transcription and are believed to be responsible for some of the anti-inflammatory activity of endogenously administered glucocorticoids. In addition, glucocorticoids may also exert physiologic effects independent of nuclear transcription. Biologically relevant glucocorticoid receptor agonists include cortisol and corticosterone. Many synthetic glucocorticoid receptor agonists exist including dexamethasone, prednisone and prednisolone.

Glucocorticoid Receptor Antagonists

Glucocorticoid receptor antagonists bind to the receptor and prevent glucocorticoid receptor agonists from binding and eliciting GR mediated events, including transcription. RU486 is an example of a non-selective glucocorticoid receptor antagonist.

Compounds having high glucocorticoid receptor binding affinity and, in addition, high in vivo anti-glucocorticoid activity, while having, for example, low androgenic and progestagenic activities are disclosed in U.S. Pat. No. 6,011,025, incorporated herein by reference in its entirety. ORG 34517 is an example of a compound with high glucocorticoid receptor binding affinity while having low androgenic and progestagenic activities.

It has been found that 11-(substituted phenyl)-estra-4,9-diene derivatives of formula I

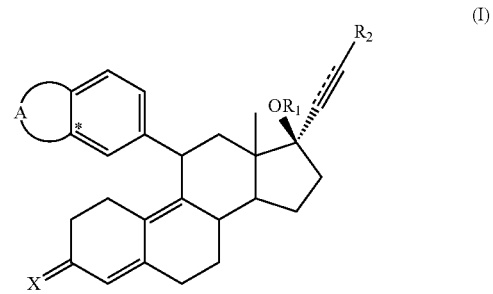

wherein
A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond, show specific and high glucocorticoid receptor binding affinity and are highly active in vivo showing predominant anti-glucocorticoid activity.

The compounds lack appreciable affinity for mineralocorticoid, progesterone, estrogen and androgen receptors, indicating a clean side effect profile.

The 11-(substituted phenyl)-estra-4,9-diene derivatives of the invention can be used in the prevention and treatment of glucocorticoid dependent diseases or symptoms, like Cushing syndrome, diabetes, glaucoma, sleep disturbances, depression, anxiety, atherosclerosis, hypertension, adiposity, osteoporosis and withdrawal symptoms from narcotics and their mixtures.

Preferred compounds according to this invention are 11-(substituted phenyl)estra-4,9-diene derivatives, wherein the heteroatom(s) are (is) O, the 5- or 6-membered ring being optionally substituted with one or more fluorine atoms; R1 is H; and X is O or NOH. More preferred compounds are 11-(substituted phenyl)estra-4,9-diene derivatives wherein A is a residue of a 5-membered ring. Particularly preferred are 11-(substituted phenyl)estra-4,9-diene derivatives wherein A contains 2 heteroatoms being O.

Especially preferred are 11-(substituted phenyl)estra-4,9-diene derivatives wherein R2 is methyl and the interrupted line represents a bond.

The most preferred compound is (11β,17β)-11-(1,3-benzodioxol-5-yl)-17-hydroxy-17-(1-propynyl)estra-4,9-dien-3-one (ORG 34517).

ORG 34517

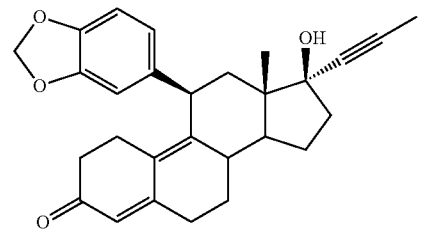

The term halogen means a fluorine, chlorine, bromine or iodine atom. Fluorine is the preferred halogen in ring A and when R2 is halogen, chlorine is preferred.

The terms (1-4C)alkyl and (1-8C)alkyl, as used in the definitions of R1 and R2, respectively, mean alkyl groups having 1-4 and 1-8 carbon atoms, respectively, for example methyl, ethyl, propyl, isopropyl, butyl, sec-butyl, tert-butyl, pentyl, neopentyl, hexyl, octyl.

The 11-(substituted phenyl)-estra-4,9-diene derivatives according to the present invention can be prepared by a process wherein a compound of formula II

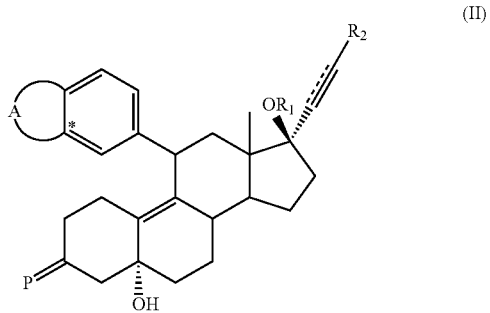

wherein A, R2 and the interrupted line have the meanings as previously defined, R1 is H, and P is a protected keto-group, is dehydrated and deprotected, after which the 17β-OH is optionally esterified by reaction with an appropriate carboxylic acid to give a derivative wherein R1 is 1-oxo(1-4C)alkyl, and optionally the 3-oxo group is converted into the corresponding 3-hydroxy- or 3-oxime derivative. The 3-oxo group can be reduced to form the 3-hydroxy-derivative by using a suitable reducing agent, such as sodium borohydride. The 3-oxime derivatives can be prepared by hydroxylamine treatment in a suitable solvent, like pyridine.

The derivatives of formula II may be prepared according to well known methods described and used for the preparation of steroids.

A suitable process for the preparation of derivatives of formula II starts from estra-4,9-diene-3,17-dione. Selective reduction of the 17-keto group to 17β-OH, 17α-H, e.g. with sodium borohydride, followed by protection of the 3-keto group, e.g., by ketalisation with ethyleneglycol, triethylorthoformate and p-toluenesulfonic acid, and oxidation of the 17-hydroxy group, e.g. with pyridinium chlorochromate, provides the 3-ketoprotected estra-5(10),9(11)-diene-3,17-dione. Alkynylation at the 17-position (yielding a 17α-alkynyl, 17β-OH derivative), followed by epoxidation of the 5(10) double bond, e.g. with hydrogen peroxide, trifluoroacetophenone, and pyridine in dichloromethane according to the method as disclosed in European patent application EP 0 298 020, provides the 3-ketoprotected 5α,10α-epoxy-17α-alkynyl-17β-hydroxy-estr-9(11)-ene-3-one.

Subsequently, compounds of formula II are formed from this epoxide derivative, for example by reaction with an organometallic compound of the formula

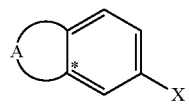

wherein X is a (alkali)metal, like lithium, or a magnesiumhalide, preferably magnesium bromide.

Suitable protective groups and methods to remove these groups are known in the art, for example from T. W. Green: Protective Groups in Organic Synthesis (Wiley, N Y, 1981). Particularly suitable protective groups for the protection of keto groups are acetals, e.g. 1,2-ethylene ketal.

The specificity of ORG 34517 for GR blockade, without significant cross-binding to other related steroidal hormone receptors (such as those for estrogen and progesterone), eliminates the likelihood of significant toxicities and side effects. Indeed, none were identified in all the substantial phase I and phase II clinical trials that already have been performed with the compound. Because the drug is envisioned as being used in limited dosing over time, coordinated with the intermittent dosing strategies typical for chemotherapeutic agents, the GR blockade also would not lead to significant alteration of HPA-axis functioning, with rapid restitution of the HPA-axis to baseline following dosing.

Formulations

The compounds of the invention may be administered enterally or parenterally. Mixed with pharmaceutically suitable auxiliaries, e.g., as described in the standard reference, Gennaro et al., Remington's Pharmaceutical Sciences. The compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation or eye drops, or as a spray, e.g. for use as a nasal spray.

For making dosage units, e.g., tablets, the use of conventional additives such as fillers, colorants, polymeric binders and the like is contemplated. In general, any pharmaceutically acceptable additive which does not interfere with the function of the active compounds can be used. Suitable carriers with which the compositions can be administered include lactose, starch, cellulose derivatives and the like, or mixtures thereof, used in suitable amounts.

Dosage Forms

The compositions of the present invention can be processed by agglomeration, air suspension chilling, air suspension drying, balling, coacervation, coating, comminution, compression, cryopelletization, encapsulation, extrusion, wet granulation, dry granulation, homogenization, inclusion complexation, lyophilization, melting, microencapsulation, mixing, molding, pan coating, solvent dehydration, sonication, spheronization, spray chilling, spray congealing, spray drying, or other processes known in the art. The compositions can be provided in the form of a minicapsule, a capsule, a tablet, an implant, a troche, a lozenge (minitablet), a temporary or permanent suspension, an ovule, a suppository, a wafer, a chewable tablet, a quick or fast dissolving tablet, an effervescent tablet, a buccal or sublingual solid, a granule, a film, a sprinkle, a pellet, a bead, a pill, a powder, a triturate, a platelet, a strip or a sachet. Compositions can also be administered as a "dry syrup", where the finished dosage form is placed directly on the tongue and swallowed or followed with a drink or beverage. These forms are well known in the art and are packaged appropriately. The compositions can be formulated for oral, nasal, buccal, ocular, urethral, transmucosal, vaginal, topical or rectal delivery.

The pharmaceutical composition can be coated with one or more enteric coatings, seal coatings, film coatings, barrier coatings, compress coatings, fast disintegrating coatings, or enzyme degradable coatings. Multiple coatings can be applied for desired performance. Further, the dosage form can be designed for immediate release, pulsatile release, controlled release, extended release, delayed release, targeted release, synchronized release, or targeted delayed release. For release/absorption control, solid carriers can be made of various component types and levels or thicknesses of coats, with or without an active ingredient. Such diverse solid carriers can be blended in a dosage form to achieve a desired performance. The definitions of these terms are known to those skilled in the art. In addition, the dosage form release profile can be affected by a polymeric matrix composition, a coated matrix composition, a multiparticulate composition, a coated multiparticulate composition, an ion-exchange resin-based composition, an osmosis-based composition, or a biodegradable polymeric composition. Without wishing to be bound by theory, it is believed that the release may be effected through favorable diffusion, dissolution, erosion, ion-exchange, osmosis or combinations thereof.

When formulated as a capsule, the capsule can be a hard or soft gelatin capsule, a starch capsule, or a cellulosic capsule. Although not limited to capsules, such dosage forms can further be coated with, for example, a seal coating, an enteric coating, an extended release coating, or a targeted delayed release coating. These various coatings are known in the art, but for clarity, the following brief descriptions are provided: seal coating, or coating with isolation layers: Thin layers of up to 20 microns in thickness can be applied for variety of reasons, including for particle porosity reduction, to reduce dust, for chemical protection, to mask taste, to reduce odor, to minimize gastrointestinal irritation, etc. The isolating effect is proportional to the thickness of the coating. Water soluble cellulose ethers are preferred for this application. HPMC and ethyl cellulose in combination, or Eudragit E100, may be particularly suitable for taste masking applications. Traditional enteric coating materials listed elsewhere can also be applied to form an isolating layer.

Extended release coatings are designed to effect delivery over an extended period of time. The extended release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended release dosage forms can be readily designed by one skilled in art to achieve delivery to both the small and large intestines, to only the small intestine, or to only the large intestine, depending upon the choice of coating materials and/or coating thickness.

Enteric coatings are mixtures of pharmaceutically acceptable excipients which are applied to, combined with, mixed with or otherwise added to the carrier or composition. The coating may be applied to a compressed or molded or extruded tablet, a gelatin capsule, and/or pellets, beads, granules or particles of the carrier or composition. The coating may be applied through an aqueous dispersion or after dissolving in appropriate solvent. Additional additives and their levels, and selection of a primary coating material or materials will depend on the following properties: 1. resistance to dissolution and disintegration in the stomach; 2. impermeability to gastric fluids and drug/carrier/enzyme while in the stomach; 3. ability to dissolve or disintegrate rapidly at the target intestine site; 4. physical and chemical stability during storage; 5. non-toxicity; 6. easy application as a coating (substrate friendly); and 7. economical practicality.

Dosage forms of the compositions of the present invention can also be formulated as enteric coated delayed release oral dosage forms, i.e., as an oral dosage form of a pharmaceutical composition as described herein which utilizes an enteric coating to affect release in the lower gastrointestinal tract. The enteric coated dosage form may be a compressed or molded or extruded tablet/mold (coated or uncoated) containing granules, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

Delayed release generally refers to the delivery so that the release can be accomplished at some generally predictable location in the lower intestinal tract more distal to that which would have been accomplished if there had been no delayed release alterations. The preferred method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. Polymers for use in the present invention are anionic carboxylic polymers.

Shellac, also called purified lac, a refined product obtained from the, resinous secretion of an insect. This coating dissolves in media of pH>7.

Colorants, detackifiers, surfactants, antifoaming agents, lubricants, stabilizers such as hydroxy propyl cellulose, acid/base may be added to the coatings besides plasticizers to solubilize or disperse the coating material, and to improve coating performance and the coated product.

In carrying out the method of the present invention, the combination of the invention may be administered to mammalian species, such as dogs, cats, humans, etc. and as such may be incorporated in a conventional systemic dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid of sodium bisulfate) or the like.

The dose administered must be carefully adjusted according to age, weight and condition of the patient, as well as the route of administration, dosage form and regimen and the desired result.

The pharmaceutical compositions of the invention may be administered in the dosage forms in single or divided doses of one to four times daily. It may be advisable to start a patient on a low dose combination and work up gradually to a high dose combination.

Tablets of various sizes can be prepared, e.g., of about 1 to 2000 mg in total weight, containing one or both of the active pharmaceutical ingredients, with the remainder being a physiologically acceptable carrier of other materials according to accepted pharmaceutical practice. These tablets can be scored to provide for fractional doses. Gelatin capsules can be similarly formulated.

Liquid formulations can also be prepared by dissolving or suspending one or the combination of active substances in a conventional liquid vehicle acceptable for pharmaceutical administration so as to provide the desired dosage in one to four teaspoonfuls.

Dosage forms can be administered to the patient on a regimen of, for example, one, two, three, four, five, six, or other doses per day In order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms in a manner similar to that described above.

In formulating the compositions, the active substances, in the amounts described above, may be compounded according to accepted pharmaceutical practice with a physiologically acceptable vehicle, carrier, excipient, binder, preservative, stabilizer, flavor, etc., in the particular type of unit dosage form.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, aspartame, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dosage unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

One embodiment of this invention includes methods of treating, preventing, or diagnosing a particular disease or condition by administering the disclosed nanoparticles, composite nanoparticles, nanosuspension, or nanocapsules to a subject. In many instances, the nanoparticles, composite nanoparticles, or nanocapsules are administered alone or can be included within a pharmaceutical composition. An effective amount of a pharmaceutical composition, generally, is defined as that amount sufficient to ameliorate, reduce, minimize, or limit the extent of the disease or condition. More rigorous definitions may apply, including elimination, eradication, or cure of the disease or condition.

"Nanoparticles" are solid particles of an average particle diameter of, for example, less than about 1 micron (micrometer). One micron is 1,000 nanometers (nm).

"Stabilized" nanoparticles are nanoparticles coated with a stabilizing material and having a reduced tendency for aggregation and loss of dispersion with respect to nanoparticles of the compound of the invention without a stabilizing coating.

A nano-spray is a spray containing nanoparticles or a spray that produces nanoparticles. A nanodispersion is a dispersion containing nanoparticles. A nanosuspension is a suspension containing nanoparticles.

The liquid formulations useful herein may comprise a solvent, solution, suspension, microsuspension, nanosuspension, emulsion, microemulsion, gel or even a melt containing the active component or components. In some embodiments the nanoparticles, nanofibers, or nanofibrils may be in the form of, or within or on, granules, powders, suspensions, solutions, dissolvable films, mats, webs, tablets, or releasable forms particularly releasable dosage forms. Other particular useful forms are concentrates to which a diluting liquid is added prior to use. The product may also be sprayed onto the inner surface of a container to which a liquid is added later prior to use and the nanoparticles, nanofibers, or nanofibrils, are released into the liquid.

Pharmaceutical compositions of the present invention can include nanoparticles, composite nanoparticles, nanosuspension, or nanocapsules of the present invention.

In certain non-limiting embodiments, pharmaceutical compositions may comprise, for example, at least about 0.1% of an active ingredient or nanoparticles, composite nanoparticles, or nanocapsules, for example. In other embodiments, the an active ingredient or nanoparticles, composite nanoparticles, or nanocapsules may comprise between about 2% to about 75% of the weight of the unit, or between about 25% to about 60%, for example, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered.

The composition may also include various antioxidants to retard oxidation of one or more active ingredient or nanoparticles, composite nanoparticles, nanosuspension, or nanocapsules. The prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In order to increase the effectiveness of a treatment with the nanoparticles, nanogels, composite nanoparticles, nanosuspension, or nanocapsules of the present invention, it may be desirable to combine these nanoparticles, composite nanoparticles, or nanocapsules with other therapies effective in the treatment of a particular disease or condition.

The formulations as described above may be administered for a prolonged period, that is, for as long as the potential for a disease or condition remains or the symptoms continue.

Packaging/Treatment Kits

The present invention relates to a kit for conveniently and effectively carrying out the methods in accordance with the present invention. Such kits may be suited for the delivery of solid oral forms such as tablets or capsules. Such a kit may include a number of unit dosages. Such kits can include a means for containing the dosages oriented in the order of their intended use. An example of a means for containing the dosages in the order of their intended uses is a card. An example of such a kit is a "blister pack". Blister packs are well known in the packaging industry and are widely used for packaging pharmaceutical unit dosage forms. If desired, the blister can be in the form of a childproof blister, i.e., a blister that is difficult for a child to open, yet can be readily opened by an adult. If desired, a memory aid can be provided, for example in the form of numbers, letters, or other markings or with a calendar feature and/or calendar insert, designating the days and the sections of a day in the treatment schedule in which the dosages can be administered, such as an AM dose is packaged with a "mid day" and a PM dose; or an AM dose is packaged with a PM dose. Alternatively, placebo dosages, or vitamin or dietary supplements, either in a form similar to or distinct from the pharmaceutical active dosages, can be included.

In one aspect, the package, kit or container comprises a "blister package" (also called a blister pack, or bubble pack). In one aspect, the blister package consists of two or more separate compartments: Am dosage of this invention, and PM dosage of this invention, or mid-day dosage of this invention. This blister package is made up of two separate material elements: a transparent plastic cavity shaped to the product and its blister board backing. These two elements are then joined together with a heat sealing process which allows the product to be hung or displayed. Exemplary types of "blister packages" include: Face seal blister packages, gang run blister packages, mock blister packages, interactive blister packages, slide blister packages.

Blister packs, clamshells or trays are forms of packaging used for goods; thus, the invention provides for blister packs, clamshells or trays comprising a composition (e.g., a (the multi-ingredient combination of drugs of the invention) combination of active ingredients) of the invention. Blister packs, clamshells or trays can be designed to be non-reclosable, so consumers can tell if a package has already opened. They are used to package for sale goods where product tampering is a consideration, such as the pharmaceuticals of the invention. In one aspect, a blister pack of the invention comprises a moulded PVC base, with raised areas (the "blisters") to contain the tablets, pills, etc. comprising the combinations of the invention, covered by a foil laminate. Tablets, pills, etc. are removed from the pack either by peeling the foil back or by pushing the blister to force the tablet to break the foil. In one aspect, a specialized form of a blister pack is a strip pack.

In one aspect, a blister pack also comprises a method of packaging where the compositions comprising combinations of ingredients of the invention are contained in-between a card and a clear PVC. The PVC can be transparent so the item (pill, tablet, geltab, etc.) can be seen and examined easily; and in one aspect, can be vacuum-formed around a mould so it can contain the item snugly and have room to be opened upon purchase. In one aspect, the card is brightly colored and designed depending on the item (pill, tablet, geltab, etc.) inside, and the PVC is affixed to the card using pre-formed tabs where the adhesive is placed. The adhesive can be strong enough so that the pack may hang on a peg, but weak enough so that this way one can tear open the join and access the item. Sometimes with large items or multiple enclosed pills, tablets, geltabs, etc., the card has a perforated window for access. In one aspect, more secure blister packs, e.g., for items such as pills, tablets, geltabs, etc. of the invention are used, and they can comprise of two vacuum-formed PVC sheets meshed together at the edges, with the informative card inside.

In one aspect, blister packaging comprises at least two components (e.g., is a multi-ingredient combination of drugs of the invention): a thermoformed "blister" which houses the product (e.g., a pharmaceutical combination of the invention), and then a "blister card" that is a printed card with an adhesive coating on the front surface. During the assembly process, the blister component, which is most commonly made out of PVC, is attached to the blister card using a blister machine. This machine introduces heat to the flange area of the blister which activates the glue on the card in that specific area and ultimately secures the PVG blister to the printed blister card. The thermoformed PVG blister and the printed blister card can be as small or large. Conventional blister packs can also be sealed (e.g., using an AERGO 8 DUO®, SCA Consumer Packaging, Inc., DeKalb, Ill.) using regular heat seal tooling. This alternative aspect, using heat seal tooling, can seal common types of thermoformed packaging.

As discussed herein, the products of manufacture of the invention can comprise the packaging of the therapeutic drug combinations of the invention, alone or in combination, as "blister packages" or as a plurality of packettes, including as lidded blister packages, lidded blister or blister card or packets, or a shrink wrap.

In one aspect, laminated aluminum foil blister packs are used, e.g., for the preparation of drugs designed to dissolve immediately in the mouth of a patient. This exemplary process comprises having the drug combinations of the invention prepared as an aqueous solution(s) which are dispensed (e.g., by measured dose) into an aluminum (e.g., alufoil) laminated tray portion of a blister pack. This tray is then freeze-dried to form tablets which take the shape of the blister pockets. The alufoil laminate of both the tray and lid fully protects any highly hygroscopic and/or sensitive individual doses. In one aspect, the pack incorporates a child-proof peel open security laminate. In one aspect, the system give tablets an identification mark by embossing a design into the alufoil pocket that is taken up by the tablets when they change from aqueous to solid state. In one aspect, individual 'push-through' blister packs/packettes are used, e.g., using hard temper aluminum (e.g., alufoil) lidding material. In one aspect, hermetically-sealed high barrier aluminum (e.g., alufoil) laminates are used. In one aspect, any of the invention's products of manufacture, including kits or blister packs, use foil laminations and strip packs, stick packs, sachets and pouches, peelable and non-peelable laminations combining foil, paper, and film for high barrier packaging.

Other means for containing said unit dosages can include bottles and vials, wherein the bottle or vial comprises a memory aid, such as a printed label for administering said unit dosage or dosages. The label can also contain removable reminder stickers for placement on a calendar or dayminder to further help the patient to remember when to take a dosage or when a dosage has been taken.

ORG 34517 Promotes Sensitivity to Chemotherapy

The glucocorticoid receptor (GR) is expressed in a subset of both ERalpha-positive and -negative human breast cancers as well as in some ovarian cancers. In vitro and in vivo experiments suggest that activation of the GR in ER-negative pre-malignant breast epithelial and cancer cells initiates cell survival pathways under stress conditions that normally induce significant cell death (e.g. chemotherapy, radiation, growth factor deprivation). Thus, GR antagonism is predicted to enhance chemotherapy sensitivity of GR+/ER– breast cancer cells by blocking stress-mediated cell survival pathways that would otherwise counteract chemotherapy-induced apoptosis.

In support of the present invention that GR activation mediates chemo-resistance (and associated increase risk of relapse for early stage ER– breast cancers), recently the association was examined between GR (NR3C1) gene expression and GR target gene expression in human ER– breast cancers and cell lines. It was found that in ER– breast cancers, high GR expression is associated with a significantly increased probability of relapse in early stage patients. This analysis and previous data in breast and ovarian cancer have led to the present invention wherein "GR high" breast tumors may respond better to cytotoxic therapies if glucocorticoid receptor (GR) antagonist therapy is administered with chemotherapy. Furthermore, GR antagonist therapy should not worsen the lymphopenia sometimes associated with taxane therapy because GR signaling is pro-apoptotic to lymphocytes.

Cancer/Tumor Stem Cells

Cancer stem cells comprise a unique subpopulation (often 0.1-10% or so) of a tumor that, relative to the remaining 90% or so of the tumor (i.e., the tumor bulk), are more tumorigenic, relatively more slow-growing or quiescent, and often relatively more chemoresistant than the tumor bulk. Given that conventional therapies and regimens have, in large part, been designed to attack rapidly proliferating cells (i.e., those cancer cells that comprise the tumor bulk), cancer stem cells which are often slow-growing may be relatively more resistant than faster growing tumor bulk to conventional therapies and regimens. Cancer stem cells can express other features which make them relatively chemoresistant such as multi-drug resistance and anti-apoptotic pathways. The aforementioned would constitute a key reason for the failure of standard oncology treatment regimens to ensure long-term benefit in most patients with advanced stage cancers—i.e., the failure to adequately target and eradicate cancer stem cells. In some instances, a cancer stem cell(s) is the founder cell of a tumor (i.e., it is the progenitor of the cancer cells that comprise the tumor bulk).

Cancer stem cells have been identified in a large variety of cancer types. For instance, Bonnet et al., using flow cytometry were able to isolate the leukemia cells bearing the specific phenotype CD34+CD38−, and subsequently demonstrate that it is these cells (comprising <1% of a given leukemia), unlike the remaining 99+% of the leukemia bulk, that are able to recapitulate the leukemia from which it was derived when transferred into immunodeficient mice. See, e.g., Nat Med 3:730-737 (1997). That is, these cancer stem cells were found as <1 in 10,000 leukemia cells yet this low frequency population was able to initiate and serially transfer a human leukemia into severe combined immunodeficiency/non-obese diabetic (NOD/SCID) mice with the same histologic phenotype as in the original tumor.

Cox et al. identified small subfractions of human acute lymphoblastic leukemia (ALL) cells which had the phenotypes CD34$^+$/CD10$^-$ and CD34$^+$/CD19$^-$, and were capable of engrafting ALL tumors in immunocompromised mice—i.e. the cancer stem cells. In contrast, no engraftment of the mice was observed using the ALL bulk, despite, in some cases, injecting 10-fold more cells. See Cox et al., Blood 104(19): 2919-2925 (2004).

Multiple myeloma was found to contain small subpopulations of cells that were CD138− and, relative to the large bulk population of CD138+ myeloma cells, had greater clonogenic and tumorigenic potential. See Matsui et al., "Characterization of clonogenic multiple myeloma cells," Blood 103 (6): 2332. The authors concluded that the CD138− subpopulation of multiple myeloma was the cancer stem cell population.

Kondo et al. isolated a small population of cells from a C6-glioma cell line, which was identified as the cancer stem cell population by virtue of its ability to self-renew and recapitulate gliomas in immunocompromised mice. See Kondo et al., Proc. Natl. Acad. Sci. USA 101:781-786 (2004). In this study, Kondo et al. determined that cancer cell lines contain a population of cancer stem cells that confer the ability of the line to engraft immunodeficient mice.

Breast cancers were shown to contain a small population of cells with stem cell characteristics (bearing surface markers CD44+CD24low lin−). See Al-Hajj et al., Proc. Natl. Acad. Sci. USA 100:3983-3988 (2003). As few as 200 of these cells, corresponding to 1-10% of the total tumor cell population, are able to form tumors in NOD/SCID mice. In contrast, implantation of 20,000 cells that lacked this phenotype (i.e. the tumor bulk) was unable to re-grow the tumor.

A subpopulation of cells derived from human prostate tumors was found to self-renew and to recapitulate the phenotype of the prostate tumor from which they were derived thereby constituting the prostate cancer stem cell population. See Collins et al., "Prospective Identification of Tumorigenic Prostate Cancer Stem Cells," Cancer Res 65(23):10946-10951 (2005).

Fang et al. isolated a subpopulation of cells from melanoma with cancer stem cell properties. In particular, this subpopulation of cells could differentiate and self-renew. In culture, the subpopulation formed spheres whereas the more differentiated cell fraction from the lesions were more adherent. Moreover, the subpopulation containing sphere-like cells were more tumorigenic than the adherent cells when grafted into mice. See Fang et al., "A Tumorigenic Subpopulation with Stem Cell Properties in Melanomas," Cancer Res 65(20): 9328-9337 (2005).

Singh et al. identified brain tumor stem cells. When isolated and transplanted into nude mice, the CD133+ cancer stem cells, unlike the CD133− tumor bulk cells, form tumors that can then be serially transplanted. See Singh et al., "Identification of human brain tumor initiating cells," Nature 432: 396-401 (2004); Singh et al., "Cancer stem cells in nervous system tumors," Oncogene 23:7267-7273 (2004); Singh et al., "Identification of a cancer stem cell in human brain tumors," Cancer Res. 63:5821-5828 (2003).

Since conventional cancer therapies target rapidly proliferating cells (i.e., cells that form the tumor bulk) these treatments are believed to be relatively ineffective at targeting and impairing cancer stem cells. In fact, cancer stem cells, including leukemia stem cells, have indeed been shown to be relatively resistant to conventional chemotherapeutic therapies (e.g. Ara-C, daunorubicin) as well as other targeted therapies (e.g. Gleevec®, Velcade®).

Cancer Therapies

Any therapy (e.g., therapeutic or prophylactic agent) which is useful, has been used, is currently being used, or may be used for the prevention, treatment and/or management of cancer can be used to prevent, treat, and/or manage the patient whose neoplasia and/or cancer stem cells are monitored in accordance with the methods of the invention. Also, such neoplasia and/or cancer stem cell monitoring can be employed in conjunction with any therapy for cancer according to the instant invention. Therapies (e.g., therapeutic or prophylactic agents) include, but are not limited to, peptides, polypeptides, fusion proteins, nucleic acid molecules, small molecules, mimetic agents, synthetic drugs, inorganic molecules, and organic molecules. Non-limiting examples of cancer therapies include chemotherapies, radiation therapies, hormonal therapies, anti-angiogenesis therapies, targeted therapies, and/or biological therapies including immunotherapies and surgery. In certain embodiments, a prophylactically and/or therapeutically effective regimen comprises the administration of a combination of therapies. In certain embodiments, ORG 34517 can be administered as an agent to treat or prevent neoplasia. In certain embodiments, RU486 (mifepristone) can be administered as an agent to treat or prevent neoplasia.

Examples of cancer therapies include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine (Vidaza); azetepa; azotomycin; batimastat; benzodepa; bicalutamide; bisantrene hydrochloride; bisnafide dimesylate; bisphosphonates (e.g., pamidronate (Aredria), sodium clondronate (Bonefos), zoledronic acid (Zometa), alendronate (Fosamax), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine (Ara-C); dacarbazine; dactinomycin; daunorubicin hydrochloride; decitabine (Dacogen); demethylation agents, dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; histone deacetylase inhibitors (HDAC-Is) hydroxyurea; idarubicin hydrochloride; ifosfamide; ilmofosine; imatinib mesylate (Gleevec, Glivec); interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; lenalidomide (Revlimid); letrozole; leuprolide acetate; liarozole hydrochloride; lometrexol sodium; lomustine; losoxantrone hydrochloride; masoprocol; maytansine; mechlorethamine hydrochloride; anti-CD2 antibodies (e.g., siplizumab (MedImmune Inc.; International Publication No. WO 02/098370, which is incorporated herein by reference in its entirety)); megestrol acetate; melengestrol acetate; melphalan; menogaril; mercaptopurine; methotrexate; methotrexate sodium; metoprine; meturedepa; mifepristone; mitindomide; mitocarcin; mitocromin; mitogillin; mitomalcin; mitomycin; mitosper; mitotane; mitoxantrone hydrochloride; mycophenolic acid; nocodazole; nogalamycin; ORG 34517; ormaplatin; oxaliplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; RU486; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other examples of cancer therapies include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-I; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; LFA-3TIP (Biogen, Cambridge, Mass.; International Publication No. WO 93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors;

picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; gamma secretase inhibitors, single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; anti-integrin antibodies (e.g., anti-integrin $a_v b_3$ antibodies); vorozole; zanoterone; zeniplatin; zilascorb; and zinostatin stimalamer.

A non-limiting list of compounds that could be used to target cancer stem cells includes: inhibitors of interleukin-3 receptor (IL-3R) and CD123 (including peptides, peptide-conjugates, antibodies, antibody-conjugates, antibody fragments, and antibody fragment-conjugates that target IL-3R or CD123); cantharidin; norcantharidin and analogs and derivatives thereof; Notch pathway inhibitors including gamma secretase inhibitors; sonic hedgehog/smoothened pathway inhibitors including cyclopamine and analogs thereof; antibodies to CD96; certain NF-kB/proteasome inhibitors including parthenolide and analogs thereof; certain triterpenes including celastrol; certain mTOR inhibitors; compounds and antibodies that target the urokinase receptor; sinefungin; certain inosine monophosphate dehydrogenase (IMPDH) inhibitors; PPAR-alpha and PPAR-gamma agonists and antagonists (including pioglitazone, tesaslitazar, muraglitazar, peliglitazar, lobeglitazone, balaglitazone, ragaglitazar, rosiglitazone, farglitazar, sodeiglitazar, reglitazar, naveglitazar, oxeglitazar, metaglidasen, netoglitazone, darglitazone, englitazone, thiazolidinediones, aleglitazar, edaglitazone, rivoglitazone, troglitazone, imiglitazar, and sipoglitazar); telomerase inhibitors; antibodies to EpCAM (ESA); GSK-3 beta agonists and antagonists (including Lithium, 6-bromoinirubin-3'-oxime (BIO), TDZD8); Wnt pathway inhibitors including antibodies to frizzled or small molecules that inhibit disheveled/frizzled or beta catenin; anti-CD20 antibodies and conjugates (e.g. Rituxan, Bexxar, Zevalin) for novel use in multiple myeloma or melanoma; anti-CD133 antibody; anti-CD44 antibody; antibodies to IL-4; certain differentiation agents such as versnarinone; compounds that target CD33 such as an antibody or betulinic acid; compounds that target lactadherin such as an antibody; small molecules or antibodies that target CXCR4 or SDF-1; small molecules or antibodies that target multi-drug resistance pumps; inhibitors of survivin; inhibitors of XIAP; small molecules that target Bcl-2; antibodies to CLL-1; and furin inhibitors (such as cucurbitacins).

An additional non-limiting list of compounds that could also be used to target cancer and/or cancer stem cells includes: i) antibodies, antibody fragments, and proteins that are either naked or conjugated to a therapeutic moiety that target certain cell surface targets on cancer stem cells, or ii) small molecules known in the art including ones that can be further optimized (e.g., via chemistry) or identified via a cancer stem cell-based screen (e.g., such as one that would determine whether a compound impairs proliferation or viability of a cancer stem cell through standard methods, the cell surface and intracellular targets including (not meant to be exhaustive) are: Rex1 (Zfp42), CTGF, Activin A, Wnt, FGF-2, HIF-1, AP-2gamma, Bmi-1, nucleostemin, hiwi, Moz-TIF2, Nanog, beta-arrestin-2, Oct-4, Sox2, stella, GDF3, RUNX3, EBAF, TDGF-1, nodal, ZFPY, PTNE, Evi-1, Pax3, Mcl-1, c-kit, Lex-1, Zfx, lactadherin, aldehyde dehydrogenase, BCRP, telomerase, CD133, Bcl-2, CD26, Gremlin, and FoxC2.

In some embodiments, the therapy(ies) is an immunomodulatory agent. Non-limiting examples of immunomodulatory agents include proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamides (e.g., leflunamide), T cell receptor modulators, cytokine receptor modulators, and modulators mast cell modulators. Other examples of immunomodulatory agents can be found, e.g., in U.S. Publication No. 2005/0002934 A1 at paragraphs 259-275 which is incorporated herein by reference in its entirety. In one embodiment, the immunomodulatory agent is a chemotherapeutic agent. In an alternative embodiment, the immunomodulatory agent is an immunomodulatory agent other than a chemotherapeutic agent. In some embodiments, the therapy(ies) used in accordance with the invention is not an immunomodulatory agent.

In some embodiments, the therapy(ies) is an anti-angiogenic agent. Non-limiting examples of anti-angiogenic agents include proteins, polypeptides, peptides, fusion proteins, antibodies (e.g., human, humanized, chimeric, monoclonal, polyclonal, Fvs, ScFvs, Fab fragments, F(ab)$_2$ fragments, and antigen-binding fragments thereof) such as antibodies that specifically bind to TNF-alpha, nucleic acid molecules (e.g., antisense molecules or triple helices), organic molecules, inorganic molecules, and small molecules that reduce or inhibit angiogenesis. Other examples of anti-angiogenic agents can be found, e.g., in U.S. Publication No. 2005/0002934 A1 at paragraphs 277-282, which is incorporated by reference in its entirety. In other embodiments, the therapy(ies) is not an anti-angiogenic agent.

In certain embodiments, the therapy(ies) is an alkylating agent, a nitrosourea, an antimetabolite, and anthracyclin, a topoisomerase II inhibitor, or a mitotic inhibitor. Alkylating agents include, but are not limited to, busulfan, cisplatin, carboplatin, chlorambucil, cyclophosphamide, ifosfamide, decarbazine, mechlorethamine, mephalen, and themozolomide. Nitrosoureas include, but are not limited to carmustine (BCNU) and lomustine (CCNU). Antimetabolites include but are not limited to 5-fluorouracil, capecitabine, methotrexate, gemcitabine, cytarabine, and fludarabine. Anthracyclins include but are not limited to daunorubicin, doxorubicin, epirubicin, idarubicin, and mitoxantrone. Topoisomerase II inhibitors include, but are not limited to, topotecan, irinotecan, etopiside (VP-16), and teniposide. Mitotic inhibitors include, but are not limited to taxanes (paclitaxel, docetaxel), and the vinca alkaloids (vinblastine, vincristine, and vinorelbine). In some embodiments of the invention, the therapy(ies) includes the administration cantharidin or an analog thereof. The invention includes the use of agents that target cancer stem cells. In certain embodiments, the agent acts alone. In other embodiments, the agent is attached directly or indirectly to another therapeutic moiety. Non-limiting examples of therapeutic moieties include, but are not limited to alkylating agents, anti-metabolites, plant alkaloids, cytotoxic agents, chemotherapeutic agents (e.g., a steroid, cytosine arabinoside, fluoruracil, methotrexate, aminopterin, mitomycin C, demecolcine, etoposide, mithramycin, calicheamicin, CC-1065, chlorambucil or melphalan), radionuclides, therapeutic enzymes, cytokines, toxins including plant-derived toxins, fungus-derived toxins, bacteria-derived toxin (e.g., deglycosylated ricin A chain, a ribosome inactivating protein, alpha-sarcin, aspergillin, restirictocin, a ribonuclease, a diphtheria toxin, Pseudomonas exotoxin, a bacterial endotoxin or the lipid A moiety of a bacterial endotoxin), growth modulators and RNase. In some embodiments, the agent used is an agent that binds to a marker, e.g., an antigen on a cancer stem cell. In a specific embodiment, the agent binds to an antigen that is expressed at a greater level on cancer stem cells than on normal stem cells. In a specific embodiment, the agent binds specifically to a cancer stem cell antigen that is not a normal stem cell. In other embodiments, the therapy(ies) is an agent that binds to a marker on cancer stem cells. In one embodiment, the agent that binds to a marker on cancer stem cells is an antibody or an antibody conjugated to a therapeutic moiety or an antibody fragment conjugated to a therapeutic moiety.

For example, in a specific embodiment, the agent binds specifically to the IL-3 Receptor (IL-3R). In some embodiments, the agent that binds to the IL-3R is an antibody or an antibody fragment that is specific for IL-3R. In some embodiments, the antibody or antibody fragment is conjugated either chemically or via recombinant technology to a therapeutic moiety (e.g., a chemotherapeutic agent, a plant-, fungus- or bacteria-derived toxin, a radionuclide) using a linking agent to effect a cell killing response. In certain embodiments, the antibody, antibody-conjugate, antibody fragment, or antibody fragment-conjugate binds to the .alpha.-subunit of IL-3R (i.e., the CD123 antigen). In other embodiments, the antibody, antibody-conjugate, antibody fragment, or antibody fragment-conjugate binds to the IL-3R, containing both the .alpha. and .beta. subunits. Methods for preparing antibodies to IL-3R and mimetics of antibodies to IL-3R are described in U.S. Pat. No. 6,733,743 B2, which is incorporated herein by reference in its entirety.

In other embodiments, the agent that binds to a marker on cancer stem cells is a ligand. In some embodiments, the ligand is a cytokine that binds to a cytokine receptor on cancer stem cells. In a particular embodiment, the ligand is interleukin-3 (IL-3) which can be conjugated to a therapeutic moiety that includes a chemotherapeutic agent, a plant-, fungus-, or bacteria-derived toxin, or a radionuclide. The IL-3-conjugate prophylactic and/or therapeutic therapy or regimen can be in the form of a recombinant fusion protein in embodiments where the conjugate is a toxin and the toxin is a protein, such as diphtheria toxin. Methods for preparing and isolating an IL-3-diphtheria toxin fusion protein (IL3DT) are described in Frankel et al., "Diphtheria toxin fused to human interleukin-3 is toxic to blasts from patients with myeloid leukemias," Leukemia 14:576 (2000) and Urieto et al., Protein Expression and Purification 33: 123-133 (2004), the disclosures of which are incorporated by reference in their entireties.

In certain embodiments, antibodies or fragments thereof that bind to a marker on cancer stem cells are substantially non-immunogenic in the treated subject. Methods for obtaining non-immunogenic antibodies include, but are not limited to, chimerizing the antibody, humanizing the antibody, and isolating antibodies from the same species as the subject receiving the therapy. Antibodies or fragments thereof that bind to markers in cancer stem cells can be produced using techniques known in the art. See, for example, paragraphs 539-573 of U.S. Publication No. 2005/0002934 A1, which is incorporated by reference in its entirety.

In some embodiments, the therapy comprises the use of X-rays, gamma rays and other sources of radiation to destroy cancer stem cells and/or cancer cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed inside the body close to cancer stem cells, cancer cells and/or a tumor mass.

In some embodiments, the therapy used is a proliferation based therapy. Non-limiting examples of such therapies include a chemotherapy and radiation therapy as described supra.

Currently available therapies and their dosages, routes of administration and recommended usage are known in the art and have been described in such literature as the Physician's Desk Reference (60th ed., 2006).

In a specific embodiment, cycling therapy involves the administration of a first cancer therapeutic for a period of time, followed by the administration of a second cancer therapeutic for a period of time, optionally, followed by the administration of a third cancer therapeutic for a period of time and so forth, and repeating this sequential administration, i.e., the cycle in order to reduce the development of resistance to one of the cancer therapeutics, to avoid or reduce the side effects of one of the cancer therapeutics, and/or to improve the efficacy of the cancer therapeutics.

When two prophylactically and/or therapeutically effective regimens are administered to a subject concurrently, the term "concurrently" is not limited to the administration of the cancer therapeutics at exactly the same time, but rather, it is meant that they are administered to a subject in a sequence and within a time interval such that they can act together (e.g., synergistically to provide an increased benefit than if they were administered otherwise). For example, the cancer therapeutics may be administered at the same time or sequentially in any order at different points in time; however, if not administered at the same time, they should be administered sufficiently close in time so as to provide the desired therapeutic effect, preferably in a synergistic fashion. The combination cancer therapeutics can be administered separately, in any appropriate form and by any suitable route. When the components of the combination cancer therapeutics are not administered in the same pharmaceutical composition, it is understood that they can be administered in any order to a subject in need thereof. For example, a first prophylactically and/or therapeutically effective regimen can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second cancer therapeutic, to a subject in need thereof. In various embodiments, the cancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the cancer therapeutics are administered within the same office visit. In another embodiment, the combination cancer therapeutics are administered at 1 minute to 24 hours apart.

In a specific embodiment, the combination therapies have the same mechanism of action. In another specific embodiment, the combination therapies each have a different mechanism of action.

Diagnostic System

The following are sample embodiments of the chemistry process configuration. They each consist of a plastic cartridge or glass reaction vessel with reagent dispensed inside. The user will remove the seal from the cap on the reaction vessel, insert the high void volume swab with saliva sample into cartridge or glass reaction vessel and place the assay solution into the portable fluorescent polarization apparatus for mixing with reagent one and two for rapid response to determine the level of the constituent e.g., salivary cortisol.

The invention will be illustrated in more detail with reference to the following Examples, but it should be understood that the present invention is not deemed to be limited thereto.

EXAMPLES

Example 1

This study is performed to obtain evidence for enhancement of chemotherapy sensitivity of GR+/ER−/PR−/Her2-neu-breast cancer cells by blocking stress-mediated cell survival pathways with a GR antagonist. In the present pilot study, the GR antagonist ORG 34517, is investigated, in one dose, in combination with the chemotherapeutic agent Taxol. Both the Taxol and ORG 34517 doses are selected based on previous experiments.

Materials and Methods—1×107 TNBC (Triple Negative Breast Cancer; MDA-MB-231) cells in 50 ul of PBS (phosphate buffered saline) are injected into the mammary fat pad of 4-5 week old CB-17 SCID mice (Taconic Labs). The mice are allowed to form xenografted breast tumors of approximately 200 mm3 volume. When tumors reach an average of 200 mm3 (Week "0"), 15 mice are separated into the 3 treatment groups 1) vehicle, 2) paclitaxel (Taxol), 3) ORG 34517+paclitaxel. The used paclitaxel dose is 10 mg/kg/day dissolved in Ethanol/Sesame Oil; ORG 34517 is administered in the maximum soluble dose of 20.5 mg/kg/day dissolved in Ethanol/Castor Oil. The mice receive intraperitoneal injections (200 ul) of drugs for 5 consecutive days (day 1-5). Tumors are measured three times per week. Tumor size is both expressed as absolute volume and as relative growth in comparison to baseline (day 0).

Results—Treatment of the animals is started when the tumor has a volume of at least 100 mm3. The total experimental group consisted of 15 animals. In 6 animals the tumor growth was considered not sufficient. These animals were not treated which resulted in individual group sizes of N=3. In the control situation the tumor grows within 13 days with about 800 mm3 (see raw data). To correct for baseline differences, for each animal the relative tumor growth is calculated. Relative growth is defined as (tumor size day x−tumor size day 0)/tumor size day 0. Group averages for the relative tumor growth are depicted in FIG. 1. In the control condition (Veh/Veh) the relative growth is 379%. This growth is reduced to 183% by taxol treatment (Veh/Taxo). A further reduction of the growth is induced by the addition of ORG 34517 (517/Taxo). The relative growth of this latter group is 100%.

A repeated measures ANOVA did reveal a significant time-effect (F5,36)=2.73; p=0.035), a significant treatment effect (F(2,36)=26.86; p=0.000) and a significant interaction (F(10, 36)=2.36; p=0.029). It should be remembered that the data are not normally distributed and therefore only for descriptive purposes one-sided Student-t tests were performed and revealed a significant difference (p<0.05) on day 4 and 11 when comparing Veh/Veh and Veh/Taxo. Comparing Veh/Taxo and 517/Taxo showed significances on day 4, 7, 9 and 13. This statistical analysis should be considered explorative because of the pilot nature of the study.

Figure 2:
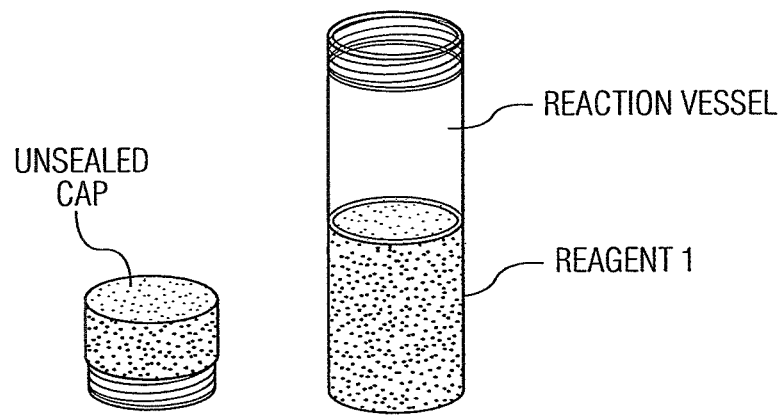
FIG. 2 is an example of glass reaction vessel with reagent one dispensed inside.
Figure 3:
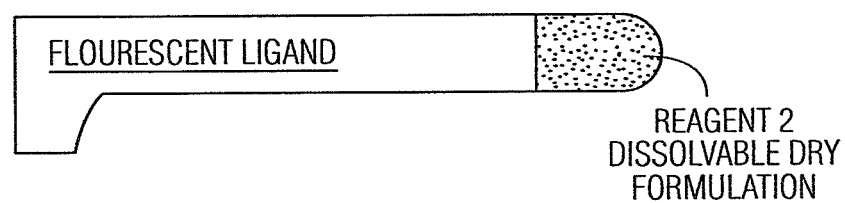
FIG. 3 is an example of a fluorescent ligand reagent two, dry formulation to be dissolved in the reaction vessel.
Figure 4A:
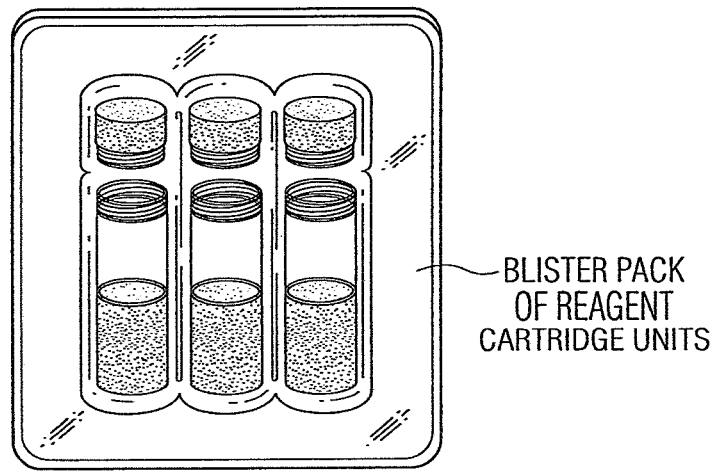
FIGS. 4A through 4D show examples of additional embodiments of the chemistry process configuration.
Figure 4B:
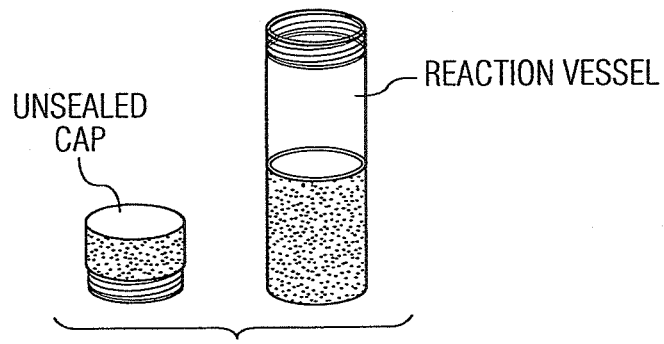
Figure 4C:
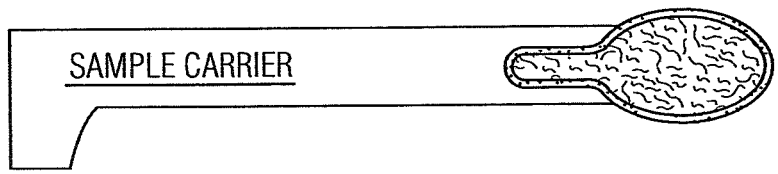
Figure 4D:
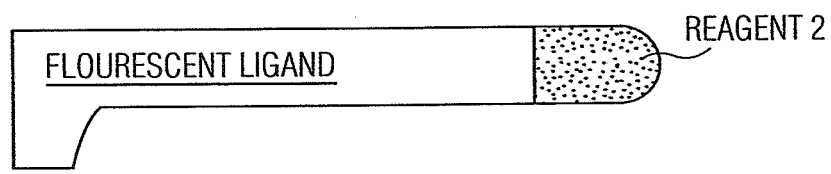
Figure 5A:
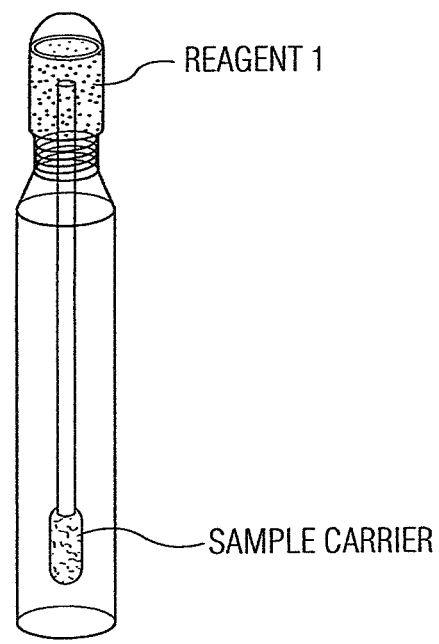
FIGS. 5A through 5C show examples of additional embodiments of the chemistry process configuration.
Figure 5B:
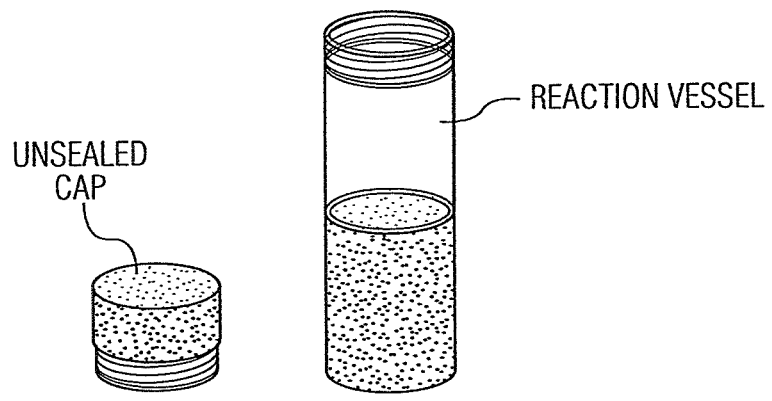
Figure 5C:
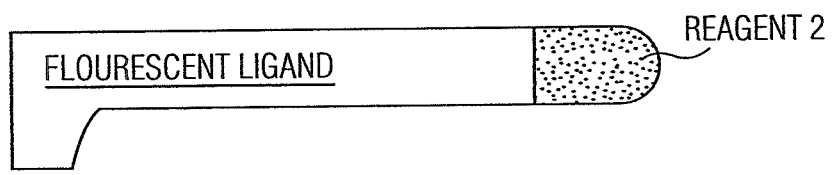
Figure 6A:
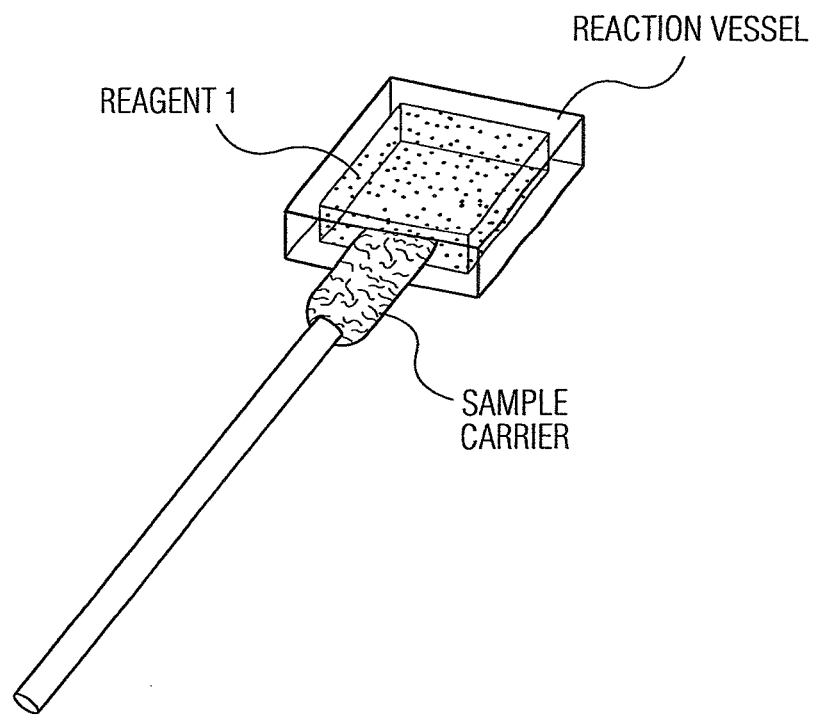
FIGS. 6A and 6B show additional embodiments of chemistry process configuration-plastic cartridge.
Figure 6B:
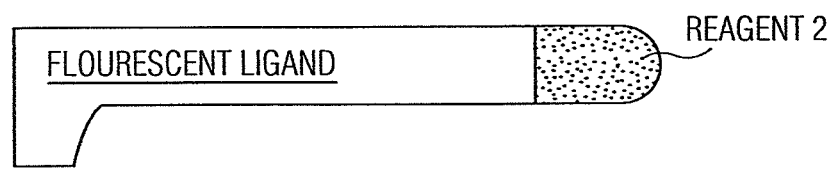
Figure 7:
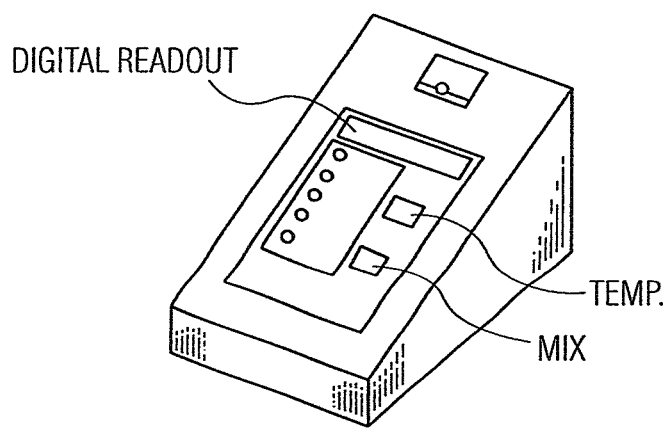
FIG. 7 is an example of a Fluorescence Polarization Reader (DC and battery operated wt.<3 lbs).
Figure 8:
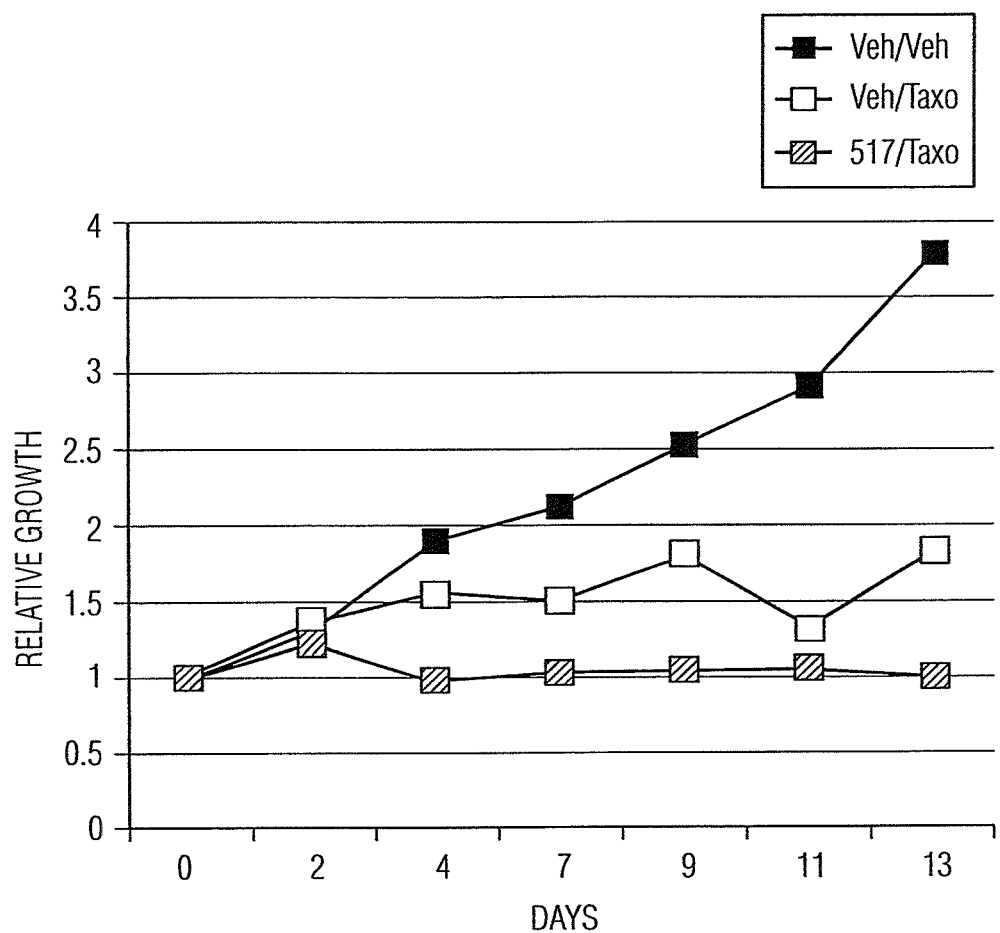
FIG. 8 is Effect of Vehicle (Ethanol/Castor Oil)/Vehicle (Ethanol/Sesame Oil), Vehicle (Ethanol/Castor Oil)/Taxol (10 mg/kg/day) and ORG 34517 (20.5 mg/kg/day)/Taxol (10 mg/kg/day) on relative tumor growth. Compounds are administered day 1-5.
Figure 9:
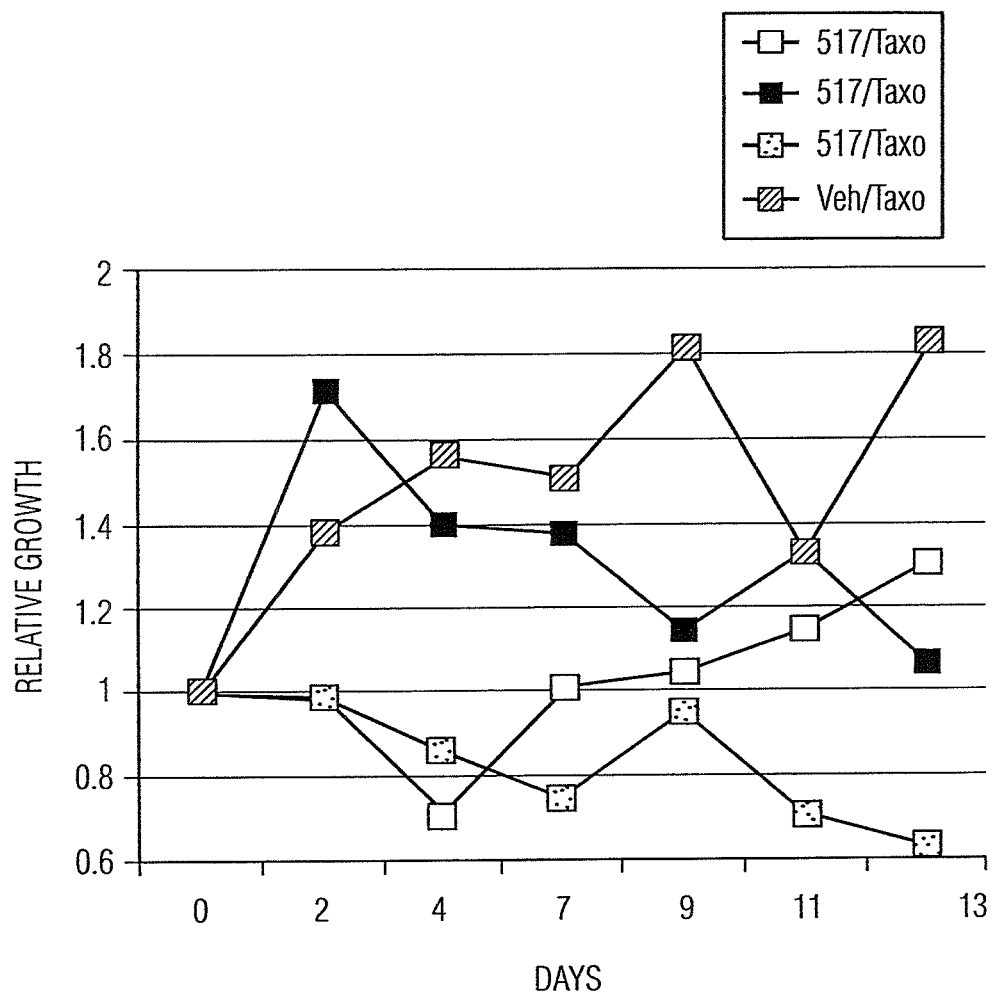
FIG. 9 shows the Effect of Vehicle (Ethanol/Castor Oil)/ Taxol (10 mg/kg/day) and ORG 34517 (20.5 mg/kg/day)/ Taxol (10 mg/kg/day) on relative tumor growth. The average curve for Veh/Taxo is shown. 517/Taxocurves are show for each individual animal. Compounds are administered day 1-5.

The individual scores for the 517/Taxo treated animals are depicted in FIG. 2. All three animals show a decreased tumor growth in comparison to Veh/Taxo treatment (mean scores). In 2 out of 3 animals a tumor shrinkage is observed, during treatment.

In this pilot study, the glucocorticoid receptor antagonist ORG 34517 (when administered intraperitoneally in a dose of 20.5 mg/kg/day for 5 days) potentiated the chemotherapeutic effect of Taxol. While Taxol injections reduced the tumor growth; Taxol+ORG 34517 induced a tumor shrinkage in 2 out of 3 animals, during treatment.

Example 2

Figure 10:
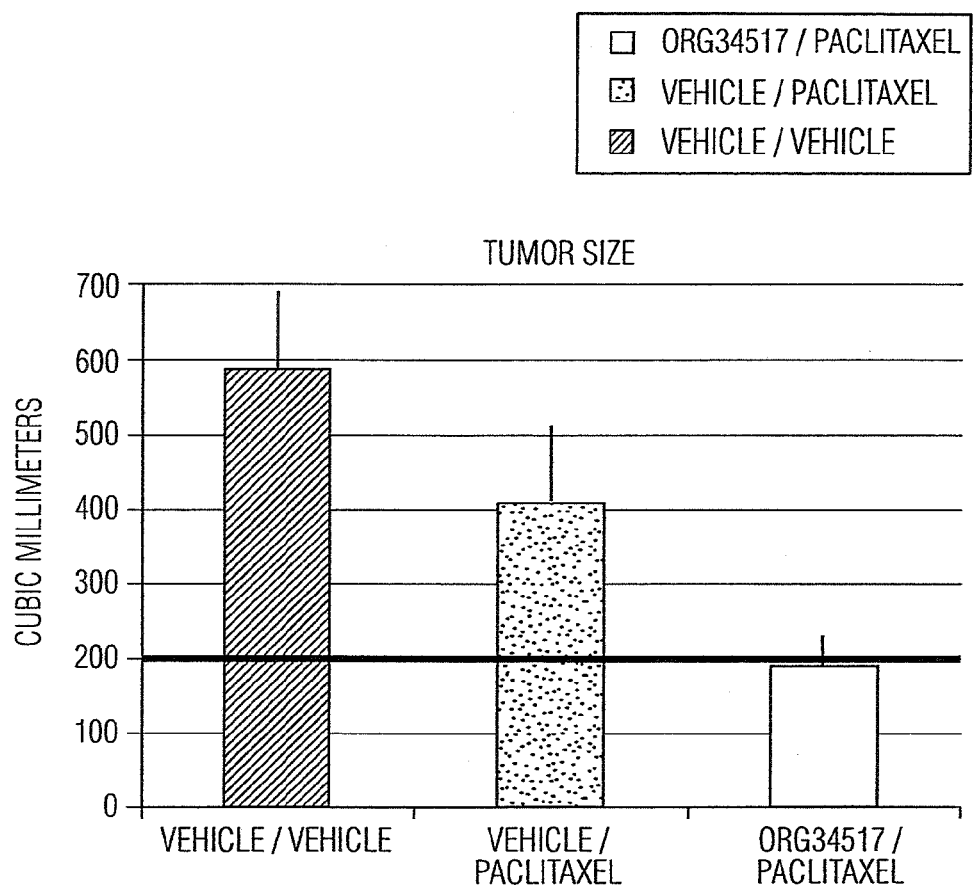
FIG. 10 shows the results of an experiment in which mice were implanted with cultured ER-GR+ human breast cancer cells. As tumor volume in each mouse approached the test threshold of 200 mm3, the mice were randomized to receive intraperitoneal injections of vehicle alone, chemotherapy (Paclitaxel) alone, and chemotherapy and ORG 34517. Each group contained 3 mice. Results show significant differences in attained tumor volume

Mice were implanted with cultured ER-GR+ human breast cancer cells. As tumor volume in each mouse approached the test threshold of 200 mm3, the mice were randomized to receive intraperitoneal injections of vehicle alone, chemotherapy (Paclitaxel) alone, and chemotherapy and ORG 34517. Each group contained 3 mice. Results show significant differences in attained tumor volume (see FIG. 10).

Example 3

In conventional dosage forms, like a capsule or a tablet (11β,17β)-11-(1,3-benzodioxol-5-yl)-17-hydroxy-17-(1-propynyl)estra-4,9-dien-3-one suffers from a low exposure, high dose variability, large food effect and non-dose linearity. Another dosage form than a conventional tablet or capsule may be able to circumvent these issues.

The solubility of (11β,17β)-11-(1,3-benzodioxol-5-yl)-17-hydroxy-17-(1-propynyl)estra-4,9-dien-3-one is determined in different solvents. These solutions can be of use for clinical treatment with the advantages as mentioned above.

TABLE 1

| Compound | Solubility |
|---|---|
| Acetone | >10 mg/mL |
| Acetonitrile | >10 mg/mL |
| Arachis oil | 2.46 mg/g |
| Benzylalcohol | 390 mg/g |
| Castor oil | 7.38 mg/g |
| Castor oil:benzylbenzoate (90:10) | 15.0 mg/g |
| Castor oil:propylene glycol laurate (0.55:0.45; v:v) | 9.4 mg/g |
| Corn oil | 2.58 mg/g |
| Cremophor EL | 23 mg/g |
| Dimethylsulfoxide | >100 mg/mL |
| Dog bile:phosphate buffer (pH = 26.5) (1:1) | ~0.08 mg/mL |
| Ethanol | >10 mg/mL |
| Ethanol:PEG 400:Propylene glycol (10:50:40) | 28.6 mg/mL |
| Ethanol:PEG 400:Propylene glycol:water (10:40:40:10) | 14.0 mg/mL |
| Gelicure 44/14 | 100 mg/mL |
| Glucofurol:water (50:50) | 0.7 mg/mL |
| Glycoferol | 118 mg/ml |
| HPβCD, 10% in water | 0.207 mg/mL |
| HPβCD, 20% in water | 0.395 mg/mL |
| HPβCD, 40% in water | 0.8 mg/mL |
| Medium Chain monoglyceride/glycerol monocaprylate | 28 mg/g |
| Methanol | >10 mg/mL |
| Miglyol 812 | 4.5 mg/g |
| Mulgofen:water (5:95) | 2 mg/mL |
| Olive oil | 2.26 mg/g |
| PEG 1500 | 37 mg/mL |
| PEG 400 | 34.4 mg/mL |
| PEG 400:Water (60:40) | 0.0006 mg/mL |
| Polysorbate in water (0.5%) | <LOD |
| Propylene glycol | 8.9 mg/mL |
| Propylene glycol | 8.9 mg/mL |
| Soy oil | 2.70 mg/g |
| Span 80 | 7 mg/g |
| TPGS:PEG 400:propyleneglycol (20:60:5) | 0.9 mg/mL |
| TPGS:PEG 400:propyleneglycol (12:17:55) | 0.7 mg/mL |
| TPGS:d-Alpha Tocopheryl Polyethylene Glycol 1000 Succinate (20%, as delivered) | 1.1 mg/mL |
| Water | 0.003 mg/mL |
| Water - Sodium lauryl sulphate (0.5% w/v) | 0.240 mg/mL |
| Water - Sodium lauryl sulphate (1.0% w/v) | 0.377 mg/mL |

Example 4

During toxicology studies also attempts were made to increase the exposure to Org 34517 (6). A rat study showed interesting results. Wistar rats 5 male and 5 female) were dosed orally with three different formulations:

a gelatin/mannitol suspension (173.6 mg/kg)

a solution of Org 34517 in arachis oil/10% benzyl alcohol (38.4 mg/kg a dispersion of Org 34517 in Gelucire 44/14 tablets (a lipid based Self Emulsifying Drug Delivery System, 7.4 mg/tablet, 37 mg/kg).

Table 2 shows the dose normalized results for Cm and AUC for the male and female rats. Although the data show a large difference between male and female rats, both the Gelucire and the Arachis oil show a much higher bioavailability than the gelatin mannitol suspension. It must be said that the data of arachis oil showed a much larger variation than the other two formulations (50% versus 10%, not shown here).

TABLE 2

Dose normalized toxicokinetic data of 3 formulations of Org 34517 in rats (M: Male, F: Female).

| | Gelucire 44/14 | Arachis oil/10% benzylalchol | Gelatin Mannitol |
|---|---|---|---|
| $C_{max}$ M [ng/mLmg Org 34517] | 3.1 | 8.2 | 0.4 |
| $C_{max}$ F [ng/mLmg Org 34517] | 42.6 | 16.8 | 3.5 |
| $AUC_{0-24}$ M [ng · hr/mLmg Org 34517] | 30.8 | 99.3 | 4.9 |
| $AUG_{0-24}$ F [ng · hr/mLmg Org 34517] | 427.4 | 231.8 | 51.7 |

The formulations which show a better bioavailability than gelatin mannitol are thought to increase the solubility of Org 34517 in the GI tract.

Figure 11:
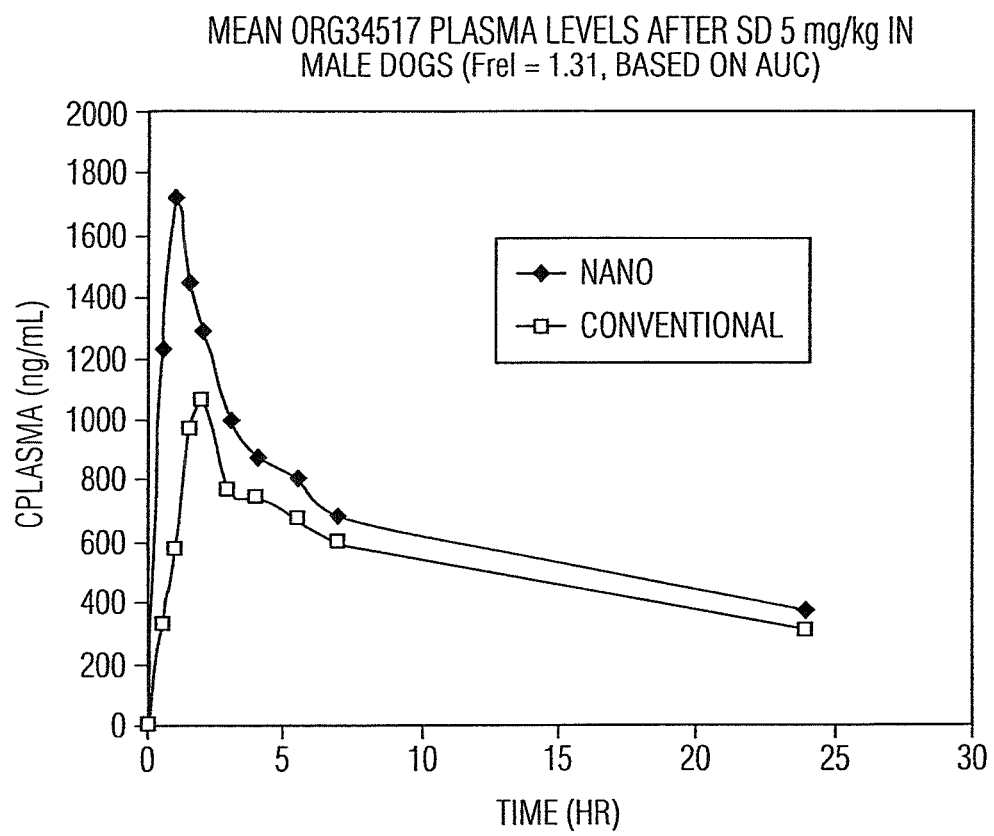
FIG. 11 shows the $AUC_{0-24}$. Two dogs were included in the test. The nanosuspension increases the exposure of (11b, 17b)-11-(1,3-benzodioxol-5-yl)-17-hydroxy-17-(1-propynyl)estra-4,9-dien-3-one.

Table 2 shows a finely milled suspension ("nanosuspension") Study in DOG, doses 5 mg/kg; 15 mg/kg; 45 mg/kg comparison of SD results. Relative bioavailability compares $AUC_{0-24}$. Two dogs were included in the test. The nanosuspension increases the exposure of (11β,17β)-11-(1,3-benzodioxol-5-yl)-17-hydroxy-17-(1-propynyl)estra-4,9-dien-3-one (see FIG. 11).

TABLE 2

Relative bioavailability in dogs: comparison of conventional suspension with finely milled suspension.

| Dose | $AUC_{0-24}$ (conventional suspension) ng * hr/mL | $AUC_{0-24}$ (finely millled suspension) ng * hr/mL | $F_{ref}$ |
|---|---|---|---|
| 5 mg/kg | 10105 | 13288 | 1.31 |
| 15 mg/kg | 21687 | 23095 | 1.06 |
| 45 mg/kg | 118493 | 90536 | 0.76 |

While the invention has been described in detail and with reference to specific examples thereof, it will be apparent to one skilled in the art that various changes and modifications can be made therein without departing from the spirit and scope thereof.

What is claimed is:

1. A method for treating neoplasia characterized by expression of a glucocorticoid receptor, in a patient in need of such treatment, comprising:

administering to said patient therapeutically effective amounts of each of:

at least one neoplasia-treating agent selected from the group consisting of taxanes, and combinations thereof; and a GCR (glucocorticoid receptor) antagonist selected from the group consisting of ORG 34517, 11-(substituted phenyl)-estra-4,9-diene derivatives, and 11-(substituted phenyl)-estra-4,9-diene derivatives of formula I

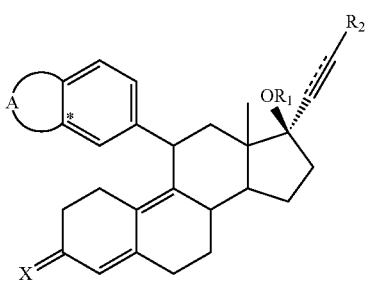

(I)

wherein A is a residue of a 5- or 6-membered ring containing 2 heteroatoms which are not connected to each other and independently selected from O and S, the ring being optionally substituted with one or more halogen atoms, or A is a residue of a 5- or 6-membered ring wherein no double C—C bonds are present, containing 1 heteroatom selected from O and S, which heteroatom is connected to the phenyl group at the position indicated with an asterisk, the ring being optionally substituted with one or more halogen atoms; R1 is H or 1-oxo(1-4C)alkyl; R2 is H, (1-8C)alkyl, halogen or CF3; X is selected from (H,OH), O, and NOH; and the interrupted line represents an optional bond, wherein the neoplasia is selected from the group consisting of hepatocellular carcinoma, breast cancer, prostate cancer, lung cancer, and ovarian cancer.

2. The method of claim 1, wherein ORG34517 is administered as an agent which directly effects tumor growth, independent of other administered treatment modalities, for palliation, remission, or cure.

3. The method of claim 1, wherein the neoplasia is chemoresistant ER/GR+ breast cancer.

4. The method of claim 1, wherein the ORG 34517 given systemically through oral or intravenous routes.

5. The method of claim 1, wherein the ORG 34517 is given to accomplish cure or remission of tumor.

6. The method of claim 1, wherein the ORG 34517 is given to accomplish reduction of tumor burden to enhance effectiveness of subsequent surgical resection.

7. The method of claim 1, wherein the ORG 34517 is given to accomplish reduction of tumor burden to make an unresectable tumor resectable.

8. The method of claim 1, wherein the taxane is selected from the group consisting of paclitaxel, docetaxel, and combinations thereof.

* * * * *